(12) United States Patent  
Kowalczyk

(10) Patent No.: US 10,426,626 B2  
(45) Date of Patent: Oct. 1, 2019

(54) BONE FIXATION DEVICE AND METHOD OF USE

(71) Applicant: Additive Orthopaedics, LLC., Little Silver, NJ (US)

(72) Inventor: Gregory J. Kowalczyk, Little Silver, NJ (US)

(73) Assignee: Additive Orthopaedics, LLC., Little Silver, NJ (US)

( * ) Notice: Subject to any disclaimer, the term of this patent is extended or adjusted under 35 U.S.C. 154(b) by 84 days.

(21) Appl. No.: 15/585,441

(22) Filed: May 3, 2017

(65) Prior Publication Data

US 2017/0319349 A1 Nov. 9, 2017

Related U.S. Application Data

(63) Continuation of application No. PCT/US2017/030701, filed on May 2, 2017.

(Continued)

(51) Int. Cl.
*A61F 2/42* (2006.01)
*A61B 17/72* (2006.01)
*A61F 2/30* (2006.01)

(52) U.S. Cl.
CPC ........ *A61F 2/4225* (2013.01); *A61B 17/7291* (2013.01); *A61F 2/30771* (2013.01);

(Continued)

(58) Field of Classification Search
CPC combination set(s) only.
See application file for complete search history.

(56) References Cited

U.S. PATENT DOCUMENTS

| 5,211,664 A | 5/1993 | Tepic et al. |
| 5,360,448 A | 11/1994 | Thramann |

(Continued)

FOREIGN PATENT DOCUMENTS

| FR | 2827157 A1 | 1/2003 |
| WO | 2012/109748 A1 | 8/2012 |

(Continued)

OTHER PUBLICATIONS

International Search Report and Written Opinion of the International Searching Authority of PCT/US17/30701, dated Aug. 3, 2017.

(Continued)

*Primary Examiner* — David H Willse
*Assistant Examiner* — Javier G Blanco
(74) *Attorney, Agent, or Firm* — Collard & Roe, P.C.

(57) ABSTRACT

An implant including a first segment at a first end, a second segment at a second end, and an intermediate segment coupled to the first segment on a first end and coupled to the second segment on a second end. The first segment may include an insertion tip at the first end of the implant and a body portion adjacent to the insertion tip, the insertion tip extending out from the body portion. The second segment may include an end member at the second end of the implant and a body portion adjacent to the end member, the end member extending out from the body portion. The second segment may include a plurality of tip portions spaced about a longitudinal axis of the second segment, and the tip portions each including at least one barb formed by a taper portion and an engagement portion extending radially into the tip portion.

8 Claims, 20 Drawing Sheets

Related U.S. Application Data

(60) Provisional application No. 62/331,086, filed on May 3, 2016.

(52) U.S. Cl.
CPC .............. *A61F 2/42* (2013.01); *A61F 2/4241* (2013.01); *A61F 2/30767* (2013.01); *A61F 2002/30013* (2013.01); *A61F 2002/3085* (2013.01); *A61F 2002/30576* (2013.01); *A61F 2002/30879* (2013.01); *A61F 2002/30892* (2013.01); *A61F 2002/30894* (2013.01); *A61F 2002/30904* (2013.01); *A61F 2002/4228* (2013.01); *A61F 2002/4243* (2013.01)

(56) References Cited

U.S. PATENT DOCUMENTS

| | | | |
|---|---|---|---|
| 5,593,446 A * | 1/1997 | Kuoni | A61F 2/3676 606/62 |
| 5,650,108 A | 7/1997 | Nies et al. | |
| 5,856,367 A | 1/1999 | Barrows et al. | |
| 5,869,080 A | 2/1999 | McGregor et al. | |
| 5,876,452 A | 3/1999 | Athanasiou et al. | |
| 6,149,688 A | 11/2000 | Brosnahan et al. | |
| 6,206,924 B1 | 3/2001 | Timm | |
| 6,228,111 B1 | 5/2001 | Toermaelae et al. | |
| 6,235,225 B1 | 5/2001 | Okada et al. | |
| 6,432,107 B1 | 8/2002 | Ferree | |
| 6,436,426 B1 | 8/2002 | Liao et al. | |
| 6,511,511 B1 | 1/2003 | Slivka et al. | |
| 6,527,810 B2 | 3/2003 | Johnson et al. | |
| 6,530,956 B1 | 3/2003 | Mansmann | |
| 6,626,945 B2 | 9/2003 | Simon et al. | |
| 6,840,960 B2 | 1/2005 | Bubb | |
| 7,235,079 B2 | 6/2007 | Jensen et al. | |
| 7,241,313 B2 | 7/2007 | Unwin et al. | |
| 7,351,280 B2 | 4/2008 | Khairoun et al. | |
| 7,578,851 B2 | 8/2009 | Dong et al. | |
| 7,879,109 B2 | 2/2011 | Borden et al. | |
| 7,892,265 B2 | 2/2011 | Perez-Cruet et al. | |
| 7,910,690 B2 | 3/2011 | Ringeisen et al. | |
| 7,943,677 B2 | 5/2011 | Papangelou et al. | |
| 8,119,152 B2 | 2/2012 | Shikinami | |
| 8,292,967 B2 | 10/2012 | Brown et al. | |
| 8,337,873 B2 | 12/2012 | Mao | |
| 8,383,024 B2 | 2/2013 | Morrissette et al. | |
| 8,389,588 B2 | 3/2013 | Ringeisen et al. | |
| 8,445,554 B2 | 5/2013 | Ringeisen et al. | |
| 8,475,505 B2 | 7/2013 | Nebosky et al. | |
| 8,500,843 B2 | 8/2013 | Grohowski | |
| 8,529,625 B2 | 9/2013 | Farrar et al. | |
| 8,535,357 B2 | 9/2013 | Stone et al. | |
| 8,657,827 B2 | 2/2014 | Fitz et al. | |
| 8,700,198 B2 | 4/2014 | Conway et al. | |
| 8,715,366 B2 | 5/2014 | Borden | |
| 2003/0009225 A1 | 1/2003 | Khandkar et al. | |
| 2003/0199875 A1 | 10/2003 | Mingozzi et al. | |
| 2004/0082999 A1 | 4/2004 | Mathys, Jr. et al. | |
| 2004/0243237 A1 | 12/2004 | Unwin et al. | |
| 2004/0258732 A1 | 12/2004 | Shikinami | |
| 2005/0187555 A1 | 8/2005 | Biedermann et al. | |
| 2006/0111715 A1 | 5/2006 | Jackson | |
| 2006/0241763 A1 | 10/2006 | Paul et al. | |
| 2006/0276788 A1 | 12/2006 | Berry et al. | |
| 2007/0156240 A1 | 7/2007 | Tsuang et al. | |
| 2007/0161985 A1 | 7/2007 | Demakas et al. | |
| 2007/0203584 A1 | 8/2007 | Bandyopadhyay et al. | |
| 2008/0132894 A1* | 6/2008 | Coilard-Lavirotte | A61B 17/1604 606/60 |
| 2008/0269893 A1 | 10/2008 | Bhatnagar et al. | |
| 2009/0187249 A1 | 7/2009 | Osman | |
| 2009/0240324 A1 | 9/2009 | Smith | |
| 2010/0042214 A1 | 2/2010 | Nebosky et al. | |
| 2010/0094420 A1 | 4/2010 | Growhowski, Jr. | |
| 2010/0249851 A1 | 9/2010 | Kay et al. | |
| 2010/0262245 A1 | 10/2010 | Alfaro et al. | |
| 2011/0004307 A1 | 1/2011 | Ahn et al. | |
| 2011/0071635 A1 | 3/2011 | Zhang et al. | |
| 2011/0172775 A1 | 7/2011 | Flickinger et al. | |
| 2011/0301709 A1 | 12/2011 | Kraus et al. | |
| 2012/0089197 A1 | 4/2012 | Anderson | |
| 2012/0271361 A1 | 10/2012 | Zhou et al. | |
| 2012/0271362 A1 | 10/2012 | Martineau et al. | |
| 2012/0330420 A1 | 12/2012 | Brodke et al. | |
| 2013/0022943 A1 | 1/2013 | Collins et al. | |
| 2013/0066435 A1 | 3/2013 | Averous et al. | |
| 2013/0090733 A1 | 4/2013 | Kraft et al. | |
| 2013/0116793 A1 | 5/2013 | Kloss | |
| 2013/0150965 A1 | 6/2013 | Taylor et al. | |
| 2013/0178900 A1 | 7/2013 | Falun et al. | |
| 2013/0211533 A1 | 8/2013 | Fonte et al. | |
| 2014/0039565 A1 | 2/2014 | Martineau et al. | |
| 2014/0107712 A1* | 4/2014 | Fallin | A61F 2/4241 606/308 |
| 2014/0107785 A1 | 4/2014 | Geisler et al. | |
| 2014/0142715 A1* | 5/2014 | McCormick | A61B 17/8883 623/21.19 |
| 2014/0180432 A1 | 6/2014 | Conway et al. | |
| 2014/0188237 A1* | 7/2014 | McCormick | A61F 5/019 623/21.19 |
| 2014/0277186 A1* | 9/2014 | Granberry | A61B 17/1682 606/301 |
| 2014/0277554 A1 | 9/2014 | Roman et al. | |
| 2014/0309747 A1* | 10/2014 | Taylor | A61F 2/42 623/21.11 |
| 2015/0032220 A1 | 1/2015 | Tyber et al. | |
| 2015/0045903 A1 | 2/2015 | Neal | |
| 2015/0088201 A1 | 3/2015 | Massoudi | |
| 2015/0100126 A1 | 4/2015 | Melkent et al. | |
| 2015/0100129 A1 | 4/2015 | Waugh et al. | |
| 2015/0142066 A1 | 5/2015 | Shemwell et al. | |
| 2015/0150607 A1 | 6/2015 | Chen et al. | |
| 2015/0230843 A1* | 8/2015 | Palmer | A61B 17/808 606/331 |
| 2015/0250513 A1 | 9/2015 | De Lavigne Sainte Suzanne | |
| 2016/0045324 A1* | 2/2016 | Austin | A61B 17/7291 623/21.19 |
| 2016/0089138 A1 | 3/2016 | Early et al. | |
| 2017/0239059 A1 | 8/2017 | Boublil et al. | |
| 2017/0245902 A1* | 8/2017 | Hollis | A61B 17/1686 |

FOREIGN PATENT DOCUMENTS

| | | |
|---|---|---|
| WO | 2014/068259 A1 | 5/2014 |
| WO | 2016/027025 A2 | 2/2016 |
| WO | 2016/177790 A1 | 11/2016 |

OTHER PUBLICATIONS

International Preliminary Report on Patentability and Written Opinion of the International Searching Authority of PCT/US17/030701, dated Nov. 6, 2018.

International Search Report and Written Opinion of the International Searching Authority of PCT/US2017/036004, dated Sep. 13, 2017.

International Search Report and Written Opinion of the International Searching Authority of PCT/US2017/044740, dated Nov. 17, 2017.

International Search Report and Written Opinion of the International Searching Authority of PCT/US2015/052121, dated Nov. 19, 2015.

* cited by examiner

BONE FIXATION DEVICE AND METHOD OF USE

CROSS REFERENCE TO RELATED APPLICATIONS

This application is a non-provisional application that claims priority from and claims the benefit of U.S. Provisional Application Ser. No. 62/331,086 titled BONE FIXATION DEVICE AND METHOD OF USE filed on May 3, 2016. This application is also a continuation application of International Application PCT/US17/30701 filed on May 2, 2017 wherein the disclosure of both of these applications are hereby incorporated by reference in their entirety.

BACKGROUND OF THE INVENTION

The present invention relates generally to general surgery, orthopaedic implants used for insertion between an interphalangeal joint. More specifically, but not exclusively, the present invention concerns an interphalangeal implant for insertion between a patient's interphalangeal joints. Digital deformities of the fingers and toes are some of the most common conditions encountered by orthopedics and podiatrists. Patient's with digital deformities often experience significant pain from structural abnormalities. Some of these abnormalities are acquired or caused by traumatic injuries, neuromuscular pathologies, systemic diseases, or mechanical problems secondary to extrinsic pressures. The deformities are popularly known as mallet finger, jersey finger, coach's finger, hammer toe, as well as a host of other names indicative of several different pathologies.

Hammer toes is generally described as an acquired disorder, typically characterized by hyperextension of the metatarsophalangeal joint (MTP joint), hyperflexion of the proximal interphalangeal joint (PIP joint), and hyperextension of the distal interphalangeal joint (DIP joint). Although this condition can be conservatively managed through the use of orthotic devices, in certain instances surgical intervention is required.

In order to prevent recurrence of the deformity and ensure the success of the surgical procedure, a PIP joint arthrodesis is typically performed. The "end-to-end" or "peg-in-hole" techniques are the most commonly used procedures. The PIP joint is aligned with the rest of the toe in a corrected anatomical position and maintained in place by the use of a 0.045 Kirschner Wire (k-wire) which is driven across the joint. Initially, the wire is placed from the PIP joint through the tip of the toe. It is then driven in retrograde fashion into the proximal phalanx. The exposed wire exiting the toe is bent to an angle greater than 90 degrees and the bent portion is cut at approximately 1 cm from the bend. At the conclusion of the surgical procedure, a small compressive dressing is placed around the toe, with a splint being used for three to four weeks to protect the pin and the toe in order to maintain correction. The k-wire and the splint are generally removed three weeks after surgery. Similar procedures may be followed to create arthrodesis of the DIP joint of the toe or for arthrodesis performed in the finger to correct digital abnormalities of the hand.

Although this type of surgical procedure has alleviated the discomfort of hammer toe and other abnormalities of the toe and finger joints for countless patients, the use of a k-wire can result in the possible post-surgical misalignment of the phalanges caused by distraction of the k-wire, as well as swelling, inflammation, and possible infection at the site of the exposed k-wire segment.

Prosthetic devices have been used to treat deformities of the finger joints. These prosthetic devices can be inserted into adjoining phalanges of the finger and can serve to function ostensibly as a normal knuckle would. Since it is generally necessary to permit one or more of the joints of the finger to flex and bend, some of these devices are slightly angled to provide for an anatomically acceptable interphalangeal joint angle of the finger. These prosthetic devices are typically made of metallic materials with smooth surface finishes, such as, that from a machining operation and finishing or polishing. While being biocompatible and inert, many of the prosthetic devices do not provide stable enough constructs and do not have a rough enough surface to promote bone growth in and around the device allowing for arthrodesis of the PIP joint. In addition, many of the devices offer surgical techniques that are complex and difficult with many steps and multiple implant or device components for implantation.

Therefore, a need exists for a bone fixation device which overcomes the above-noted problems.

SUMMARY OF THE INVENTION

Aspects of the present invention provide orthopaedic implants used for insertion between an interphalangeal joint, such as, an interphalangeal implant for insertion between a patient's interphalangeal joints.

In one aspect, provided herein is an implant, including a first segment at a first end, a second segment at a second end, and an intermediate segment coupled to the first segment on a first end and coupled to the second segment on a second end.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION FOR CARRYING OUT THE INVENTION

Figure 1:
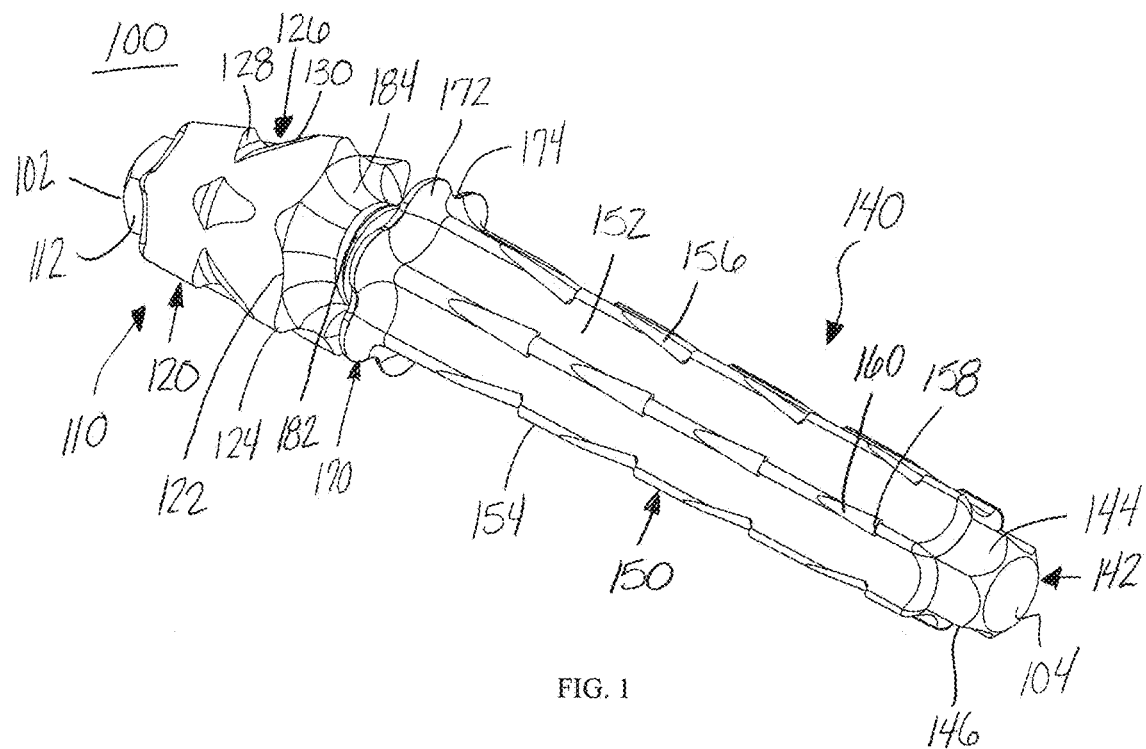
FIG. 1 is a rear perspective view of an interphalangeal implant, in accordance with an aspect of the present invention.
Figure 2:
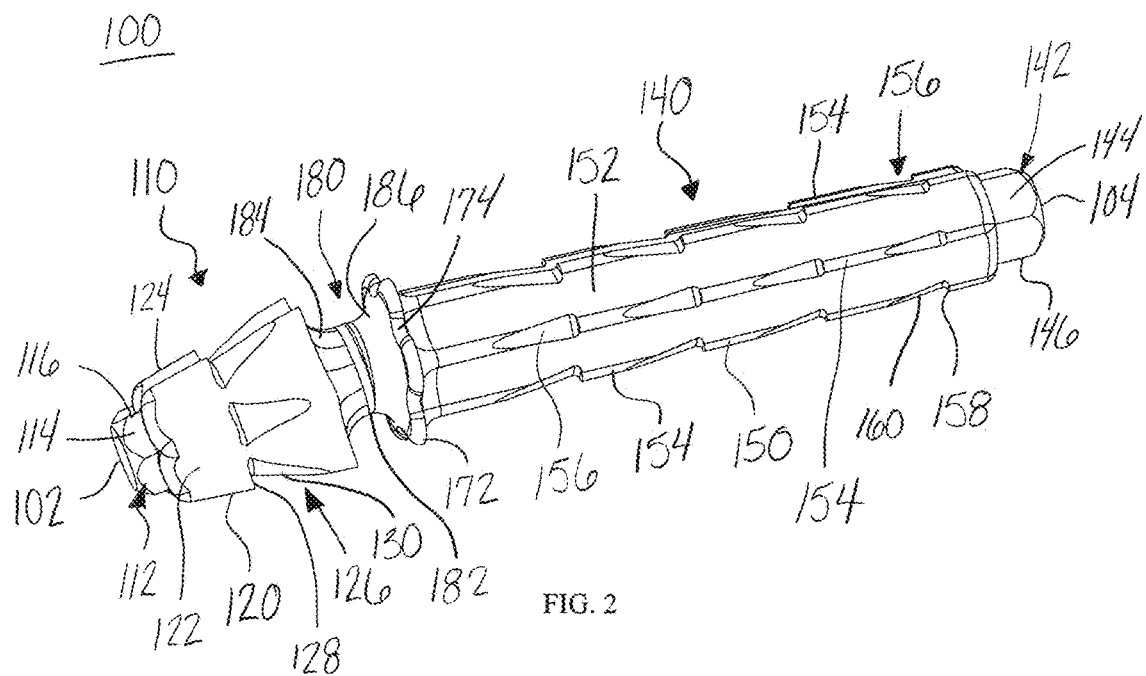
FIG. 2 is a perspective view of the implant of FIG. 1, in accordance with an aspect of the present invention.
Figure 3:
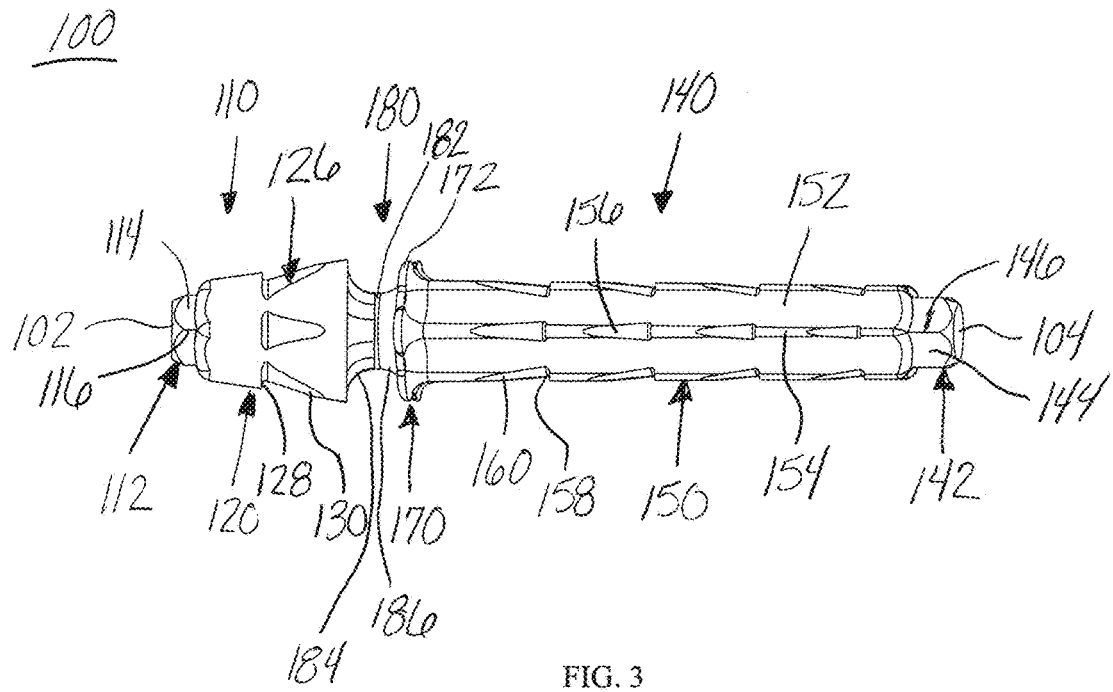
FIG. 3 is a bottom view of the implant of FIG. 1, in accordance with an aspect of the present invention.
Figure 4:
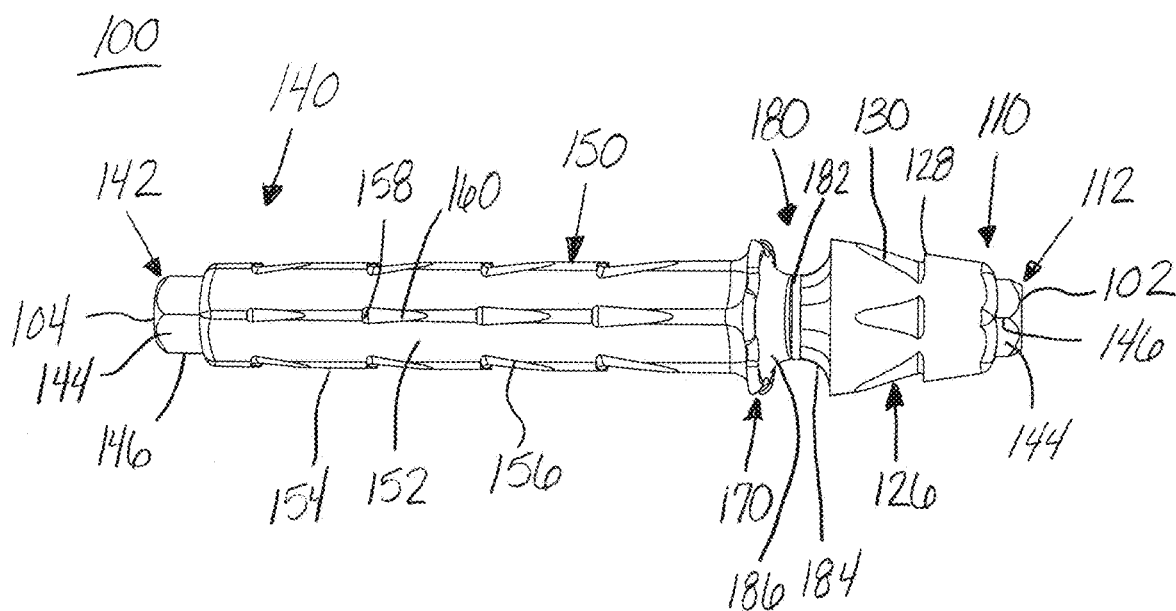
FIG. 4 is a top view of the implant of FIG. 1, in accordance with an aspect of the present invention.

Generally stated, disclosed herein are a number of embodiments of bone fixation devices. The terms "bone fixation devices," "bone fixation implants," "interphalangeal osteosynthesis devices," "interphalangeal devices," "interphalangeal implants," "devices," and "implants" may be used interchangeably as they essentially describe the same type of device. Further, a surgical methods for using the bone fixation devices are discussed. In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. In addition, for the purposes of this disclosure when referencing the device, the term "proximal" will mean the portion of the device closest or nearest the insertion instrument. The term "distal" shall mean the portion of the device farthest away from the insertion instrument.

Referring to the drawings, wherein like reference numerals are used to indicate like or analogous components throughout the several views, and with particular reference to FIGS. 1-7, there is illustrated a bone fixation implant 100. The implant 100 may have a first end 102 and a second end 104. The implant may also include a first portion or segment 110 near the first end 102 and a second portion or segment 140 near the second end 104. The first segment 110 and the second segment 140 may be, for example, coupled together with an intermediate portion or segment 180. The sizes or dimensions of the first portion 110, second portion 140 and intermediate portion 180 may vary (i.e., the size of the fixation implant 100 may vary), and may be configured for differing anatomy or patients. For example, the fixation implant 100 may be configured or provided in several different sizes. In some embodiments, the length of the implant 100 may range from about 14 mm to about 26 mm. In some embodiments, the length of the first portion 110 may range from about 9 mm to about 17 mm, the length of the second portion 140 may range from about 3 mm to about 6 mm and/or the length of the intermediate portion 180 may range from about 1 mm to about 2 mm. The width or diameter of the first portion 110 may taper from about 5 mm to about 1 mm (e.g., at an angle within the range of about 10 degrees to about 25 degrees), and/or the width or diameter of the first portion 110 may taper from about 4 mm to about ½ mm (e.g., at an angle within the range of about 0 degrees to about 5 degrees).

Figure 5:
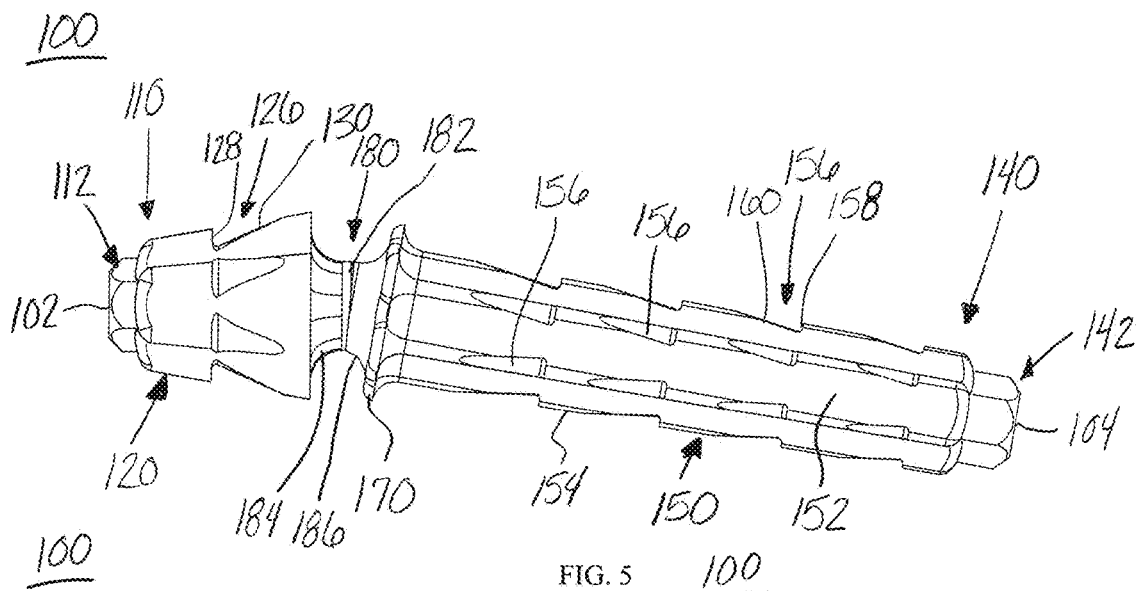
FIG. 5 is a side view of the implant of FIG. 1, in accordance with an aspect of the present invention.
Figure 6:
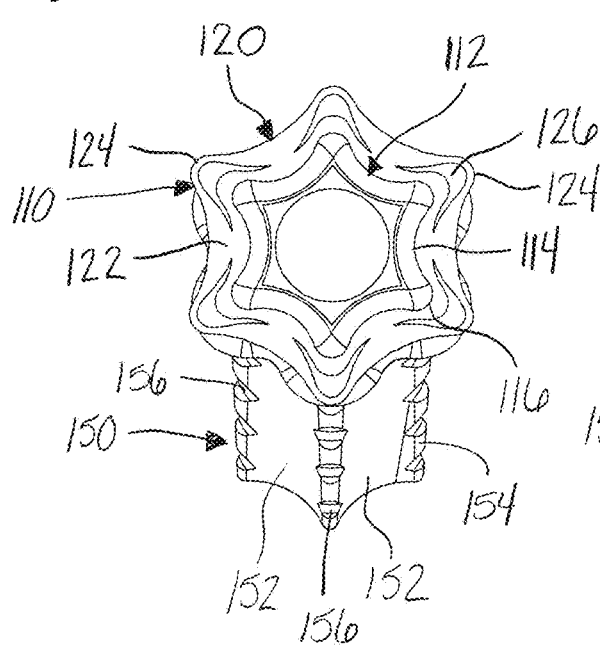
FIG. 6 is a front view of the implant of FIG. 1, in accordance with an aspect of the present invention.

With continued reference to FIGS. 1-7, the first portion 110 may include, for example, an insertion tip 112 at the first end 102 and a body portion 120 adjacent to the insertion tip 112. The insertion tip 112 may extend away from an end of the body portion 120. The width of the insertion tip 112 may be smaller than the width of the body portion 120. The insertion tip 112 may have a cross-sectional geometry or shape that is, for example, a polygonal shape, such as, a hexagonal shape, as shown in FIG. 6. The insertion tip 112 may include a plurality of side portions 114 extending between a plurality of tips 116 to form the cross-sectional shape. The plurality of side portions 114 may be, for example, curved toward a center of the first segment The insertion tip 112 may thereby form a major or maximum diameter or width, and a minor or minimum diameter or width that is less than the major or maximum diameter or width. In some embodiments, the major diameter of the insertion tip 112 may range from about 4 mm to about ½ mm, and the minor diameter of the insertion tip 112 may range from about 3 mm to about ¼ mm. In some embodiments, the major diameter of the insertion tip 112 of the implant 100 may be less than the diameter of an aperture or passageway in which the implant 100 is implanted. The plurality of tips 116 may be, for example, rounded, curved, smooth, blunt, pointed or may be sharp or angled. Although other polygonal cross-sectional shapes are contemplated, where the cross-sectional shape of the insertion tip 112 is a hexagon, the implant 100 may include, for example, six side portions 114 and six tips 116.

As shown in FIG. 6, the body portion 120 may have a cross-sectional geometry or shape that is, for example, a polygonal shape, such as a hexagon. The body portion 120 may include a plurality of side portions 122 extending between a plurality of tips 124 to form the cross-sectional shape. The plurality of side portions 122 may be, for example, curved toward a center of the first segment 110. If curved, the curvature of the plurality of side portions 122 may be configured to maximize the amount of bone and/or tissue-to-implant 100 interference to create frictional forces that impede removal of the implant 100 after implantation. The plurality of tips 124 may be, for example, rounded, curved, smooth, blunt, sharp or pointed. Although other polygonal cross-sectional shapes are contemplated, where the cross-sectional shape of the body portion 120 is a hexagon, the implant 100 may include, for example, six side portions 122 and six tips 124. As shown in FIGS. 1-5, the body portion 120 may also include at least one barb or ridge 126 inset into the body portion 120. In some embodiments, a plurality of barbs 126 may be provided and substantially aligned along a diameter of the body portion 120 at a longitudinal location of the body portion 120. In some other embodiments, the body portion 120 may include a plurality of barbs 126 provided at differing longitudinal locations on the body portion 120. The at least one barb 126 may be, for example, positioned in each tip 124. The at least one barb 126 may include an engagement portion 128 and a tapered portion 130. The engagement portion 128 may be sized and shaped for maximum contact with the intramedullary canal of the phalange to prevent pull out of the implant 100. The engagement portion 128 may be positioned, for example, closer to the first end 102 than the tapered portion 130. The tapered portion 130 may taper from the engagement portion 128 toward the second end 104. The larger the taper, the more bone and/or tissue the barb 126 may engage. The at least one barb 126 may be inset or recessed into the body portion 120 toward the interior of the implant 100. The at least one barb 126 may be inset to any degree. In some embodiments, the at least one barb 126 may be inset within the body portion 120 toward the interior of the implant 100 to a lesser extent than the neck 182 of the intermediate segment 180, as explained further below.

Figure 7:
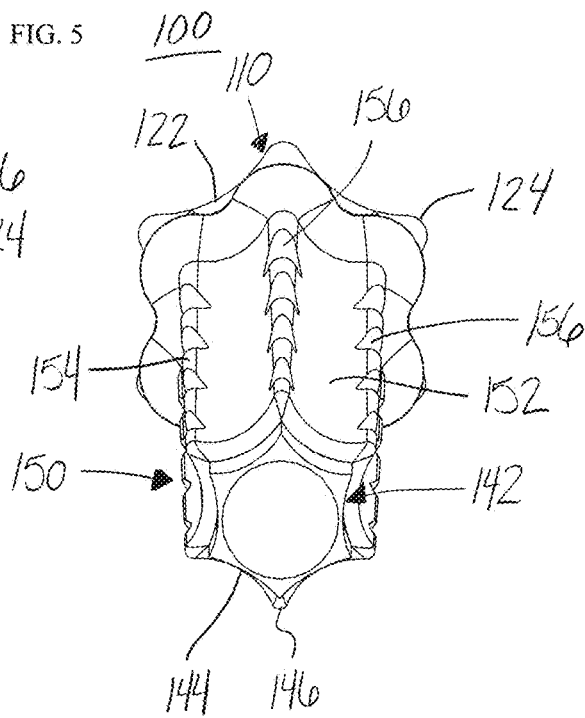
FIG. 7 is a rear view of the implant of FIG. 1, in accordance with an aspect of the present invention.

The second segment 140 may include, for example, an end member 142 at the second end 104 and a body portion 150 adjacent to the end member 142, as shown in FIGS. 1-5 and 7. The end member 142 may extend away from an end of the body portion 150. The width of the end member 142 may be smaller than the width of the body portion 150. The end member 142 may have a cross-sectional geometry or shape that is, for example, a polygonal shape, such as, a hexagon, as shown in FIG. 7. The end member 142 may include a plurality of side portions 144 extending between a plurality of tips 146 to form the cross-sectional shape. The plurality of side portions 144 may be, for example, curved toward a center of the second segment 140. If curved, the curvature of the plurality of side portions 144 may be configured to maximize the amount of bone and/or tissue-to-implant 100 interference to create frictional forces that impede removal of the implant 100 after implantation. The plurality of tips 146 may be, for example, rounded, curved, smooth, blunt, sharp or pointed. Although other polygonal cross-sectional shapes are contemplated, where the cross-sectional shape of the end member 142 is a hexagon, the implant 100 may include, for example, six end members or side portions 142 and six tips 146.

As shown in FIG. 7, the body portion 150 may have a cross-sectional geometry or shape that is, for example, a polygonal shape, such as, a hexagon. The body portion 150 may include a plurality of side portions 152 extending between a plurality of tips 154 to form the cross-sectional shape. The plurality of side portions 152 may be, for example, curved toward a center of the second segment 140. If curved, the curvature of the plurality of side portions 152 may be configured to maximize the amount of bone and/or tissue-to-implant 100 interference to create frictional forces that impede removal of the implant 100 after implantation. The plurality of tips 154 may be, for example, rounded, curved, smooth, blunt, sharp or pointed. Although other polygonal cross-sectional shapes are contemplated, where the cross-sectional shape of the body portion 150 is a hexagon, the implant 100 may include, for example, six side portions 152 and six tips 154. As shown in FIGS. 1-7, the body portion 150 may also include at least one barb or ridge 156 inset into the body portion 150. The at least one barb 156 may be, for example, positioned in each tip 154. The at least one barb 156 may include an engagement portion 158 and a tapered portion 160. The engagement portion 158 may be sized and shaped for maximum contact with the intramedullary canal of the phalange to prevent pull out of the implant 100. The engagement portion 158 may be positioned, for example, closer to the second end 104 than the tapered portion 160. The tapered portion 160 may taper from the engagement portion 158 toward the first end 102. The larger the taper of the tapered portion 160, the more bone and/or tissue the corresponding engagement portion 158 of each barb 156 may engage. The tapered portion 160 may extend into the interior of the implant 100 to any degree. In some embodiments, the tapered portion 160 may extend toward the interior of the implant 100 to a lesser extent than the neck 182 of the intermediate segment 180.

The engagement portion 158 of the at least one barb 156 may be oriented substantially perpendicular to the longitudinal direction or axis of the implant 100. Stated differently, the engagement portion 158 of the least one barb 156 may not extend toward the first end 102 or the first end 104 as it extends about the longitudinal axis or along the width of the implant 100. The engagement portion 158 of the least one barb 156 may also not extend toward the first end 102 or the second end 104 as it extends from the outer edge or surface of the tip 154 into the interior of the implant 100 (e.g., as it extends radially toward the longitudinal axis of the implant 100) to the corresponding engagement portion 158. In this way, the engagement portion 158 of the least one barb 156 may be in a straight horizontal plane along the surface of the implant 100 (e.g., oriented normal to the longitudinal axis or direction). In some embodiments, the engagement portion 158 of the least one barb 156 may be substantially planar. In other embodiments, the engagement portion 158 of the least one barb 156 may be convex or concave (in the radial direction and/or in the width direction).

The body portion 150 may include, for example, multiple barbs 156 in each tip 154 along the longitudinal axis of the body portion 150. For example, as shown in FIGS. 1-5, each tip 154 may include four barbs 156 inset into the body portion 150. The number of barbs 156 in each tip 154 may vary. The number of barbs 156 in a tip 154 may be related to the length of the tip 154. In some embodiments, adjacent barbs 156 of a tip 154 may be spaced at least about 1 mm from each other in the longitudinal direction.

The second segment 140 may also include a stop member 170 near the first end 102 of the implant 100, as shown in FIGS. 1-5. The stop member 170 may have a larger diameter than the body portion 150 and end member 142 of the second segment 140. The stop member 170 may also include a plurality of lobes 172 and a plurality of channels 174 positioned between each lobe 172, as shown in FIGS. 1 and 7. The stop member 170 may be sized and shaped larger than size and shape of an aperture or passageway in which the implant 100 is implanted, and may prevent the implant 100 from being pushed too far into the aperture or passageway. The second segment 140 may taper from the outer surface of the stop member 170 on a first side to the outer surface of the body portion 150. The taper between the stop member 170 and body portion 150 may be, for example, curved or angled.

The intermediate segment 180 may include a neck 182, a first tapered section 184 and a second tapered section 186. The first tapered section 184 may be positioned between the first segment 110 and the neck 182 and the second tapered section 186 may be positioned between the neck 182 and the second segment 140, as shown in FIGS. 2-5. The first tapered section 184 may be, for example, tapered from the outer surface of an end of the first segment 110 to the neck 182 and the taper may be, for example, curved. The second tapered section 186 may be, for example, tapered from the outer surface of a second side of the stop member 170 of the second segment 140 to the neck 182 and the taper may be, for example, curved. The intermediate segment 180 may be sized and shaped such that it maximizes the amount of bone and/or tissue to prevent pull-out of the implant 100. The intermediate segment 180 may be sized and shaped (or otherwise configured) to form a gap from bone and/or tissue such that a surgeon feels the positive force of clearing the first segment 110 and the second segment 140. The neck 182 may have a diameter smaller than the diameter of the first segment 110 and the second segment 140. As shown in FIG. 5, the intermediate segment 180 may be angled, for example, the second tapered section 186 may be angled with respect to the first tapered section 184. As also shown in FIG. 5, the implant 100 may be configured such that the first and second segments 110, 140 (or the axes thereof) are offset or angled along the longitudinal axis or direction of the implant 100 (i.e., are not collinear along the longitudinal axis or direction). Similarly, the implant 100 may be configured such that the first segment 110 and the intermediate segment 180 (or the axes thereof) are offset or angled along the longitudinal axis or direction of the implant 100 (i.e., are not collinear along the longitudinal axis or direction). For example, the first segment 110 may be angled from the intermediate segment 180 with respect to a longitudinal axis of the intermediate segment 180 or the second segment 140.

The implant 100 (e.g., the first portion 110, the second portion 140 and/or the intermediate portion 180) may be made from any material, such as any biocompatible material. In some embodiments, the implant 100 is made from titanium or PEEK. The implant 100 may be formed or manufactured utilizing any technique, such as any subtractive or additive manufacturing technique. In some embodiments, the implant 100 may be made from an additive manufacturing technique, such as being 3D printed, such that the implant 100 includes an outer surface roughness that facilitates or promotes boney ingrowth into the implant 100. In other embodiments, the outer surface roughness of the implant 100 may be produced after forming of the implant 100, such as a finishing process. The outer surface roughness of the implant 100 may also (or alternatively) act to cut or file bone (such as like a rasp) when inserted therein. The outer surface roughness of the implant 100 may thereby resist pull-out of the implant 100 after implantation. The roughness of the implant may be based upon the suitable necessary outer profile to bond with adjacent bone. For example, this surface roughness can vary such as with a substantially smooth surface having an average roughness or Ra of 0.1 microns which would be a substantially smooth surface, to a Ra of 3.61 microns which is similar to a 36-grit sandpaper. Other embodiments may include a roughness Ra of approximately 2.2 microns, or 2 microns, or 1.8 microns, or 1.5 microns, or 1 micron, or 75 microns, or 0.5 microns or lower.

It is noted that Ra is the arithmetic average of the absolute values of the profile height deviations from the mean line, recorded within the evaluation length. Simply put, Ra is the average of a set of individual measurements of a surfaces peaks and valleys. See ASME B46.1

The implant 100 (e.g., the first portion 110, the second portion 140 and/or the intermediate portion 180) may be substantially solid. In other embodiments, the implant 100 may be porous such that that the outer surface(s) of the implant 100 include pores or openings. The pores or openings of the outer surface(s) of the implant 100 (e.g., the porosity of the implant 100) may be sized and shaped to facilitate or promote boney ingrowth. In at least one additional embodiment(s), the porosity can be throughout each or any one of the first portion 110, the second portion 140 and the intermediate portion 180. Therefore, in one embodiment, the first portion 110 can be porous throughout while the second portion 140 and the intermediate portion are solid. Or alternatively the first portion 110 and the second portion 140 can be porous throughout while the intermediate portion 180 is solid, or alternatively the second portion 140 is porous throughout while the other portions are solid. In one other embodiment, the intermediate portion is porous while the first portion 110 and the second portion 140 are solid. FIGS. 28-32 show these different types of embodiments.

Referring now to FIGS. 8-11, another bone fixation implant 200 is shown. The bone fixation implant 200 is substantially similar to the implant 100 of FIGS. 1-7, and therefore the same reference numerals or like reference numerals preceded by the numeral "2" are used to indicate like elements, functions, aspects or the like (and therefore the corresponding description thereof, including alternative embodiments, presented above with respect to the implant 100 of FIGS. 1-7 may equally apply to implant 200 of FIGS. 8-11). The implant 200 may have a first end 202 and a second end 204. The implant may also include a first portion or segment 210 near the first end 202 and a second portion or segment 240 near the second end 204. The first segment 210 and the second segment 240 may be, for example, coupled together with an intermediate portion or segment 280.

With continued reference to FIGS. 8-11, the first segment 210 may be of the type described above with reference to the first segment 110 and may include, for example, an insertion tip 112 at the first end 202 and a body portion 220 adjacent to the insertion tip 112.

The insertion tip 112 may include a plurality of side portions 114 extending between a plurality of tips 116 at the first end 202, as described above with reference to implant 100 and FIGS. 1-7, which will not be described again here for brevity sake. The body portion 120 may include a plurality of side portions 122 extending between a plurality of tips 124 and at least one barb or ridge 126 inset into the body portion 120, as described above with reference to implant 100 and FIGS. 1-7, which will not be described again here for brevity sake. The at least one barb 126 may include an engagement portion 128 and a tapered portion 130, which are described in greater detail above with reference to implant 100 and which will not be described again here for brevity sake.

Figure 8:
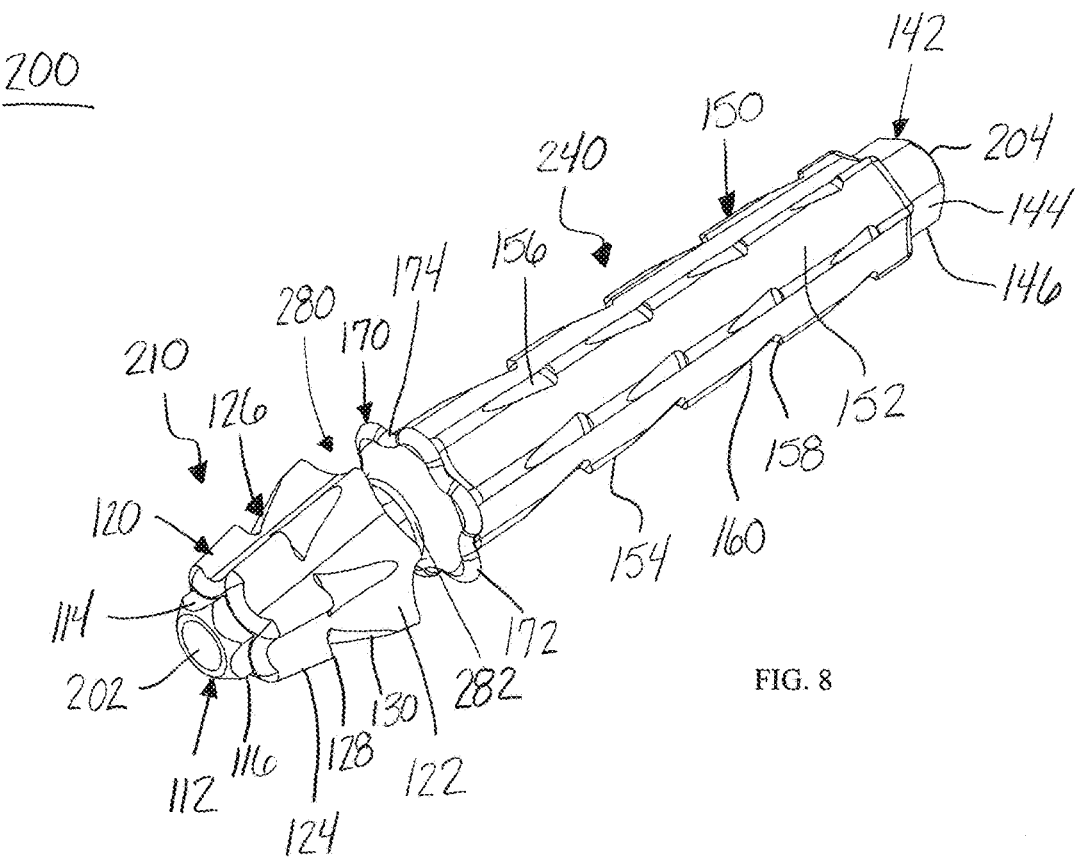
FIG. 8 is a front perspective view of another interphalangeal implant, in accordance with an aspect of the present invention.
Figure 9:
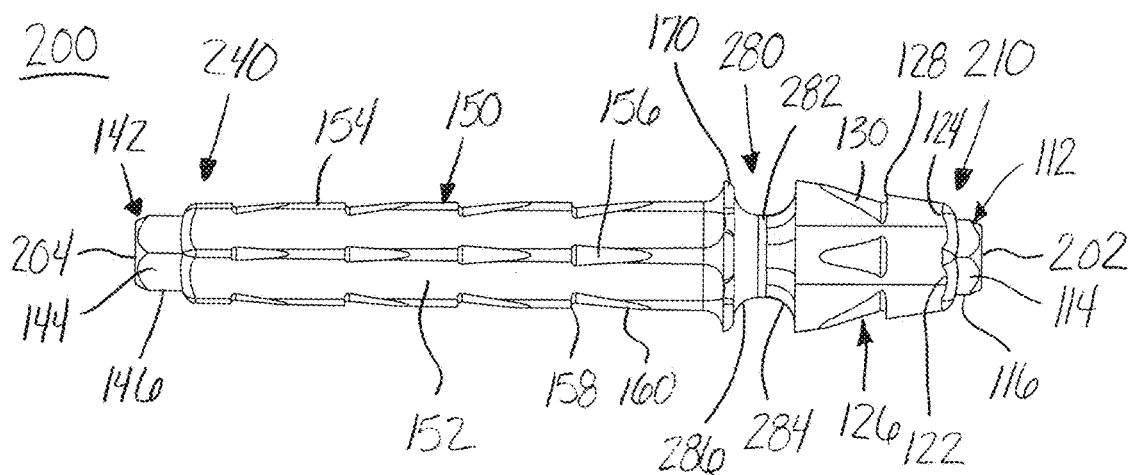
FIG. 9 is a side view of the implant of FIG. 8, in accordance with an aspect of the present invention.
Figure 10:
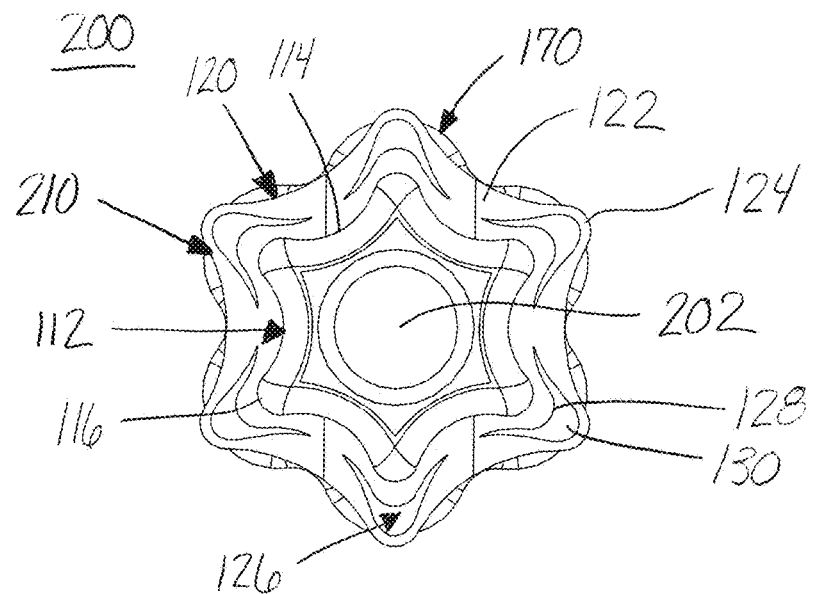
FIG. 10 is a front view of the implant of FIG. 8, in accordance with an aspect of the present invention.
Figure 11:
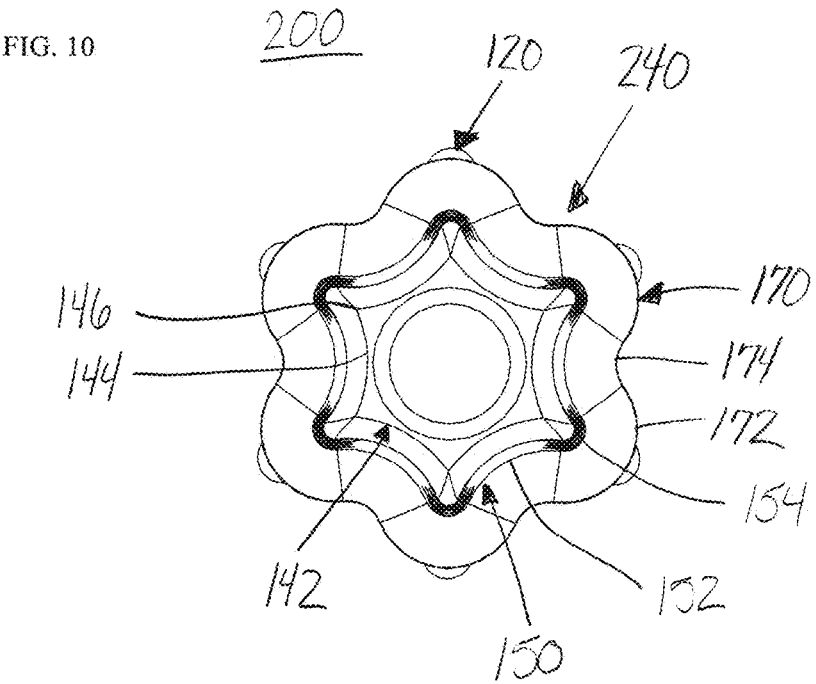
FIG. 11 is a rear view of the implant of FIG. 8, in accordance with an aspect of the present invention.

The second segment 240 may be of the type described above with reference to the second segment 140 and may include, for example, an end member 142 at the second end 204 and a body portion 150 adjacent to the end member 142, as shown in FIGS. 8 and 9. The end member 142 may include a plurality of side portions 144 extending between a plurality of tips 146, as described above with reference to implant 100 and FIGS. 1-7. The body portion 150 may include a plurality of side portions 152 extending between a plurality of tips 154 and at least one barb or ridge 156 inset into the body portion 150, as described above with reference to implant 100 and FIGS. 1-7, which will not be described again here for brevity sake. The at least one barb 156 may include an engagement portion 158 and a tapered portion 160, which are described in greater detail above with reference to implant 100 and which will not be described again here for brevity sake. The second segment 240 may also include a stop member 170 near the first end 202 of the implant 200, as shown in FIGS. 8 and 9. The stop member 170 may include a plurality of lobes 172 and a plurality of channels 174 positioned between each lobe 172 and may be of the type described above with reference to implant 100 and will not be described again here for brevity sake.

The intermediate segment 280 may include a neck 282, a first tapered section 284 and a second tapered section 286. The first tapered section 284 may be positioned between the first segment 210 and the neck 282 and the second tapered section 286 may be positioned between the neck 282 and the second segment 240, as shown in FIG. 9. The first tapered section 284 may be, for example, tapered from the outer surface of an end of the first segment 210 to the neck 282 and the taper may be, for example, curved. In other embodiments, the first tapered section 284 may be flat or linear (e.g., a 90-degree straight section). The second tapered section 286 may be, for example, tapered from the outer surface of a second side of the stop member 170 of the second segment 240 to the neck 282 and the taper may be, for example, curved. In other embodiments, the second tapered section 286 may be flat or linear (e.g., a 90-degree straight section). The neck 282 may have a diameter smaller than the diameter of the first segment 210 and the second segment 240. As shown in FIG. 9, the intermediate segment 280 is aligned along a longitudinal axis with the first and second segments 210, 240. Stated differently, the intermediate segment 280 extended linearly along the longitudinal axis or direction of the implant 200 such that the first and second segments 210, 240 (or the axes thereof) are aligned along the longitudinal axis or direction or are collinear along the longitudinal axis or direction. As noted above, the intermediate segment 180 of the implant 100 of FIGS. 1-7 is configured such that the first and second segments 110, 140 (or the axes thereof) are offset or angled along the longitudinal axis or direction of the implant 100 (i.e., are not collinear along the longitudinal axis or direction).

Referring now to FIGS. 12-17, there is illustrated a bone fixation implant 300. The bone fixation implant 300 is substantially similar to the implant 100 of FIGS. 1-7 and implant 200 of FIGS. 8-11, and therefore the same reference numerals or like reference numerals preceded by the numeral "3" are used to indicate like elements, functions, aspects or the like (and therefore the corresponding description thereof, including alternative embodiments, presented above with respect to the implant 100 of FIGS. 1-7 and implant 200 of FIGS. 8-11 may equally apply to implant 300 of FIGS. 12-17). The implant 300 may have a first end 302 and a second end 304. The implant may also include a first portion or segment 310 near the first end 302 and a second portion or segment 340 near the second end 304. The first segment 310 and the second segment 340 may be, for example, coupled together with an intermediate portion or segment 380. The implant 300 may be smaller (e.g., along the longitudinal and/or width/radial directions) than implant 100 and/or implant 200 (e.g., first segment 310, the second segment 340 and/or the intermediate segment 380 may be smaller than the respective segments of the implant 100 and/or implant 200).

Figure 14:
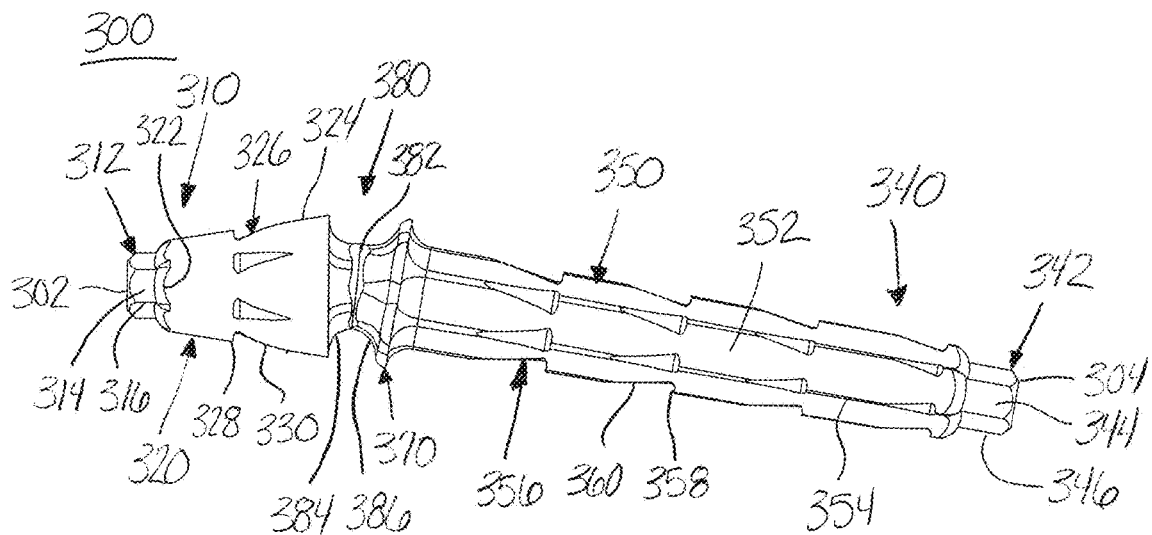
FIG. 14 is a side view of the implant of FIG. 12, in accordance with an aspect of the present invention.
Figure 15:
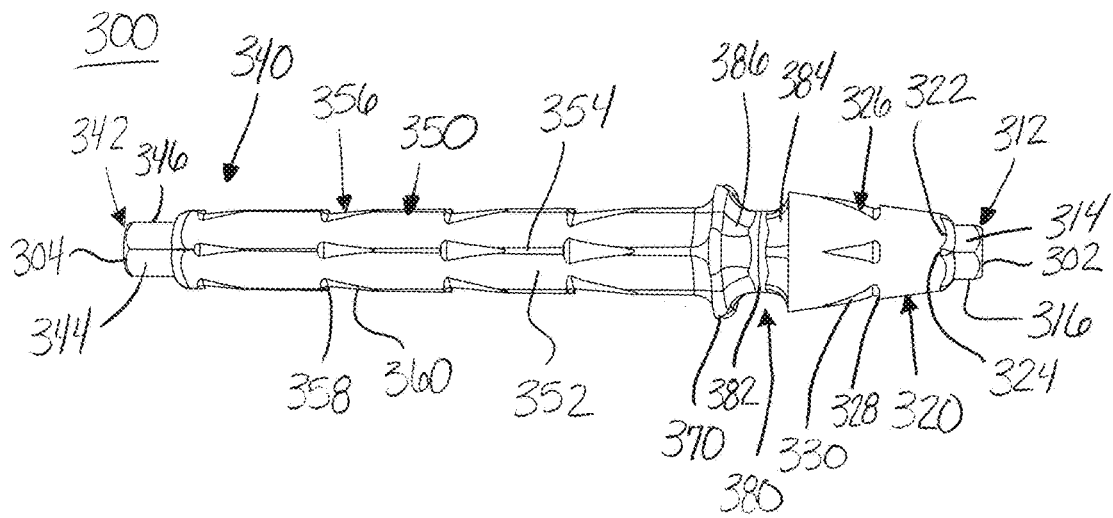
FIG. 15 is a top view of the implant of FIG. 12, in accordance with an aspect of the present invention.
Figure 16:
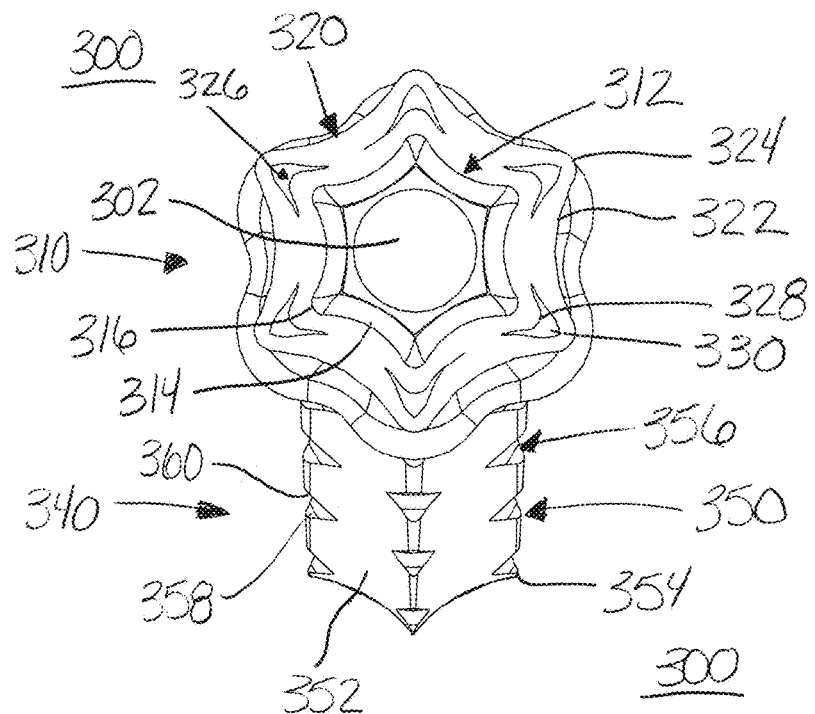
FIG. 16 is a front view of the implant of FIG. 12, in accordance with an aspect of the present invention.

With continued reference to FIGS. 12-17, the first segment 310 may include, for example, an insertion tip 312 at the first end 302 and a body portion 320 adjacent to the insertion tip 312. The insertion tip 312 may extend away from an end of the body portion 320. The width of the insertion tip 312 may be smaller than the width of the body portion 320. The insertion tip 312 may have a cross-sectional geometry or shape that is, for example, a polygonal shape, such as, a hexagonal shape, as shown in FIG. 16. The insertion tip 312 may include a plurality of side portions 314 extending between a plurality of tips 316 to form the cross-sectional shape. The plurality of side portions 314 may be, for example, curved toward a center of the first segment. If curved, the curvature of the plurality of side portions 314 may be configured to maximize the amount of bone and/or tissue-to-implant 300 interference to create frictional forces that impede removal of the implant 300 after implantation. The plurality of tips 316 may be, for example, rounded, curved, smooth, blunt, pointed or sharp. Although other polygonal cross-sectional shapes are contemplated, where the cross-sectional shape of the insertion tip 312 is a hexagon, the implant 300 may include, for example, six side portions 314 and six tips 316.

As shown in FIG. 16, the body portion 320 may have a cross-sectional geometry or shape that is, for example, a polygonal shape, such as a hexagon. The body portion 320 may include a plurality of side portions 322 extending between a plurality of tips 324 to form the cross-sectional shape. The plurality of side portions 322 may be, for example, curved toward a center of the first segment 310. If curved, the curvature of the plurality of side portions 322 may be configured to maximize the amount of bone and/or tissue-to-implant 300 interference to create frictional forces that impede removal of the implant 300 after implantation. The plurality of tips 324 may be, for example, rounded, curved, smooth, blunt, pointed or sharp. Although other polygonal cross-sectional shapes are contemplated, where the cross-sectional shape of the body portion 320 is a hexagon, the implant 300 may include, for example, six side portions 322 and six tips 324. As shown in FIGS. 12-15, the body portion 320 may also include at least one barb or ridge 326 inset into the body portion 320. In some embodiments, a plurality of barbs 326 may be provided and substantially aligned along a diameter of the body portion 320 at a longitudinal location of the body portion 320. In some other embodiments, the body portion 320 may include a plurality of barbs 326 provided at differing longitudinal locations (e.g., at differing diameters) on the body portion 320. The at least one barb 326 may be, for example, positioned in each tip 324. The at least one barb 326 may include an engagement portion 328 and a tapered portion 330. The engagement portion 328 may be sized and shaped for maximum contact with the intramedullary canal of the phalange to prevent pull out of the implant 300.

The engagement portion 328 may be positioned, for example, closer to the first end 302 than the tapered portion 330. The tapered portion 330 may taper from the engagement portion 328 toward the second end 304. The at least one barb 326 may be inset to any degree. In some embodiments, the at least one barb 326 may be inset within the body portion 320 toward the interior of the implant 300 to a lesser extent than the neck 382 of the intermediate segment 380. The larger the taper of the tapered portion 330, the more bone and/or tissue the corresponding engagement portion 328 of each barb 326 may engage. The tapered portion 330 may extend into the interior of the implant 300 to any degree. In some embodiments, the tapered portion 330 may extend toward the interior of the implant 300 to a lesser extent than the neck 382 of the intermediate segment 380.

The second segment 340 may include, for example, an end member 342 at the second end 304 and a body portion 350 adjacent to the end member 342, as shown in FIGS. 12-15 and 17.

Figure 17:
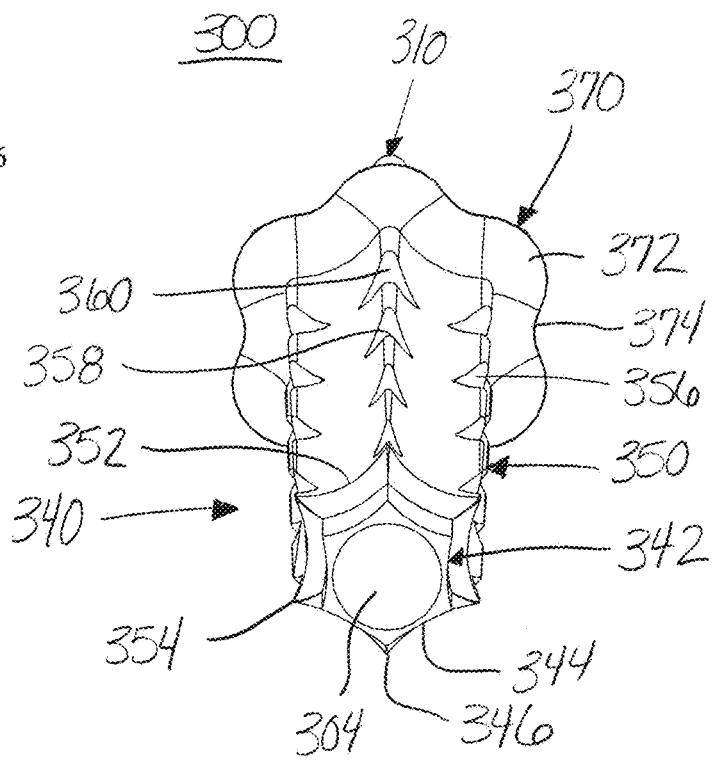
FIG. 17 is a rear view of the implant of FIG. 12, in accordance with an aspect of the present invention.

The end member 342 may extend away from an end of the body portion 350. The width of the end member 342 may be smaller than the width of the body portion 350. The end member 342 may have a cross-sectional geometry or shape that is, for example, a polygonal shape, such as, a hexagon, as shown in FIG. 17. The end member 342 may include a plurality of side portions 344 extending between a plurality of tips 346 to form the cross-sectional shape. The plurality of side portions 344 may be, for example, curved toward a center of the second segment 340. If curved, the curvature of the plurality of side portions 344 may be configured to maximize the amount of bone and/or tissue-to-implant 300 interference to create frictional forces that impede removal of the implant 300 after implantation. The plurality of tips 346 may be, for example, rounded, curved, smooth, blunt, pointed or sharp. Although other polygonal cross-sectional shapes are contemplated, where the cross-sectional shape of the end member 342 is a hexagon, the implant 300 may include, for example, six end members or side portions 342 and six tips 346.

As shown in FIG. 17, the body portion 350 may have a cross-sectional geometry or shape that is, for example, a polygonal shape, such as, a hexagon. The body portion 350 may include a plurality of side portions 352 extending between a plurality of tips 354 to form the cross-sectional shape. The plurality of side portions 352 may be, for example, curved toward a center of the second segment 340. If curved, the curvature of the plurality of side portions 352 may be configured to maximize the amount of bone and/or tissue-to-implant 300 interference to create frictional forces that impede removal of the implant 300 after implantation. The plurality of tips 354 may be, for example, rounded, curved, smooth, blunt, pointed or sharp. Although other polygonal cross-sectional shapes are contemplated, where the cross-sectional shape of the body portion 350 is a hexagon, the implant 300 may include, for example, six side portions 352 and six tips 354. As shown in FIGS. 12-17, the body portion 350 may also include at least one barb or ridge 356 inset into the body portion 350. The at least one barb 356 may be, for example, positioned in each tip 354. The at least one barb 356 may include an engagement portion 358 and a tapered portion 360. The engagement portion 358 may be sized and shaped for maximum contact with the intramedullary canal of the phalange to prevent pull out of the implant 300. The engagement portion 358 may be positioned, for example, closer to the second end 304 than the tapered portion 360. The tapered portion 360 may taper from the engagement portion 358 toward the first end 302. The at least one barb 356 may be inset to any degree. The larger the taper of the tapered portion 360 (i.e., the larger the inset of the corresponding barb 356), the more bone and/or tissue the corresponding engagement portion 358 of each barb 356 may engage. The tapered portion 360 may extend into the interior of the implant 300 to any degree. In some embodiments, the tapered portion 360 may extend toward the interior of the implant 300 to a lesser extent than the neck 382 of the intermediate segment 380. The body portion 350 may include, for example, multiple barbs 356 in each tip 354 along the longitudinal axis of the body portion 350. For example, as shown in FIGS. 12-15, each tip 354 may include four barbs 356 inset into the body portion 350.

The number of barbs 356 in each tip 354 may vary. The number of barbs 356 in a tip 354 may be related to the longitudinal length of the tip 354. In some embodiments, adjacent barbs 356 of a tip 354 may be spaced at least about 1 mm from each other in the longitudinal direction.

Figure 12:
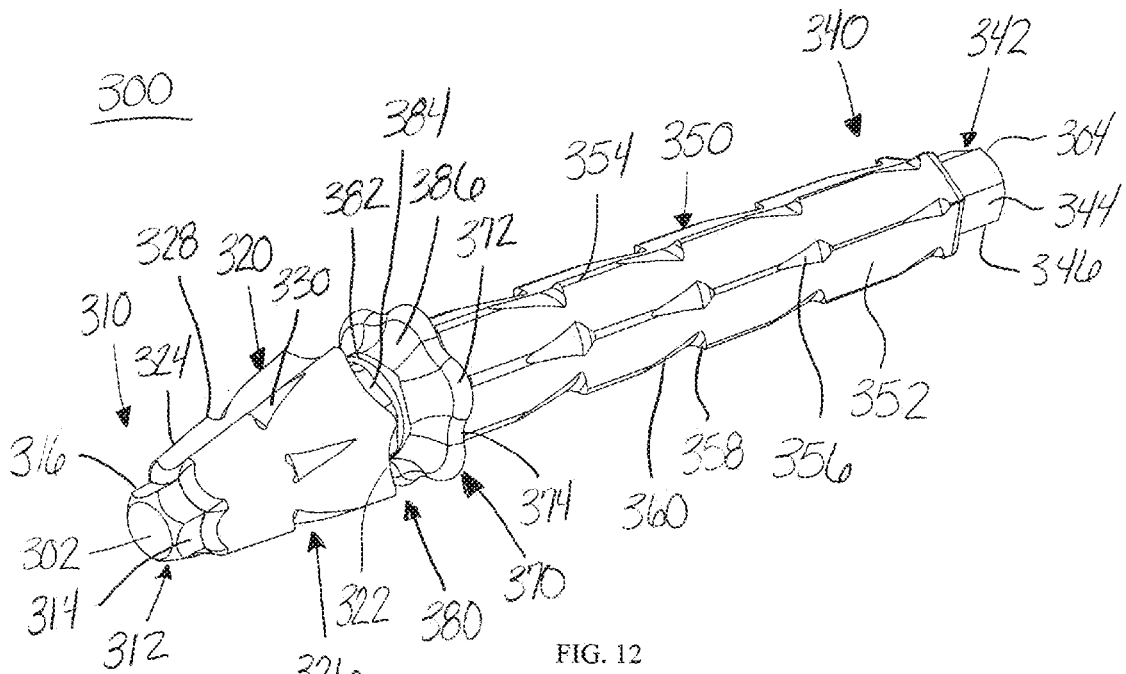
FIG. 12 is a front perspective view of another interphalangeal implant, in accordance with an aspect of the present invention.
Figure 13:
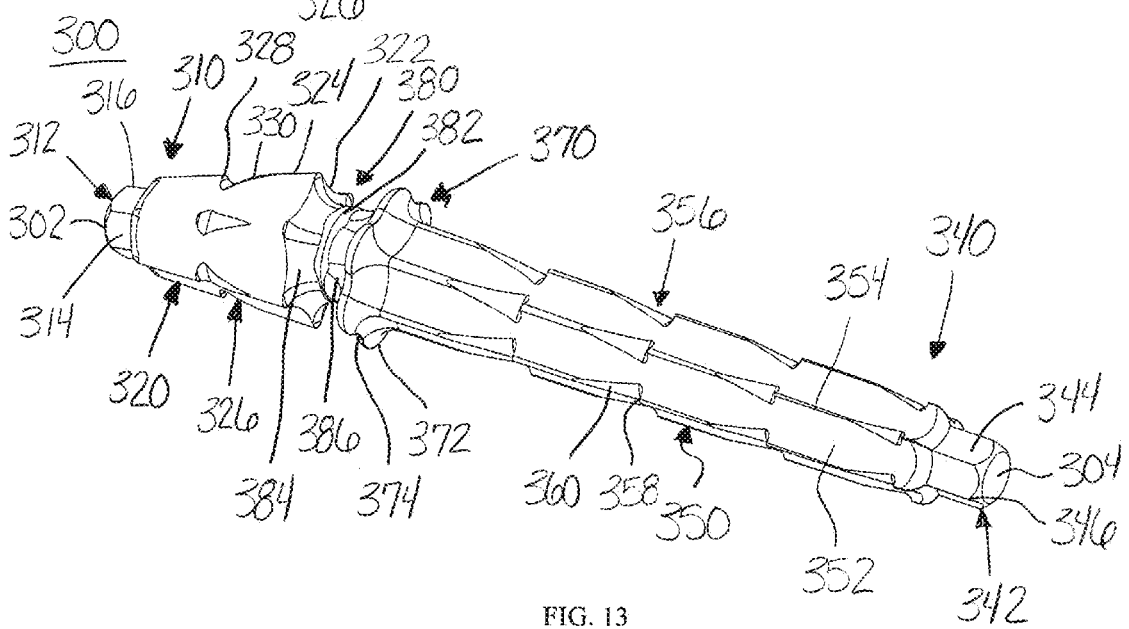
FIG. 13 is a rear perspective view of the implant of FIG. 12, in accordance with an aspect of the present invention.

The second segment 340 may also include a stop member 370 near the first end 302 of the implant 300, as shown in FIGS. 12-15. The stop member 370 may have a larger diameter than the body portion 350 and end member 342 of the second segment 340. The stop member 370 may also include a plurality of lobes 372 and a plurality of channels 374 positioned between each lobe 372, as shown in FIGS. 12-13 and 17. The stop member 370 may be sized and shaped larger than size and shape of an aperture or passageway in which the implant 300 is implanted, and may prevent the implant 300 from being pushed too far into the aperture or passageway.

The second segment 340 may taper from the outer surface of the stop member 370 on a first side to the outer surface of the body portion 350. The taper between the stop member 370 and body portion 350 may be, for example, curved or angled.

The intermediate segment 380 may include a neck 382, a first tapered section 384 and a second tapered section 386. The first tapered section 384 may be positioned between the first segment 310 and the neck 382 and the second tapered section 386 may be positioned between the neck 382 and the second segment 340, as shown in FIGS. 12-15. The first tapered section 384 may be, for example, tapered from the outer surface of an end of the first segment 310 to the neck 382 and the taper may be, for example, curved. The second tapered section 386 may be, for example, tapered from the outer surface of a second side of the stop member 370 of the second segment 340 to the neck 382 and the taper may be, for example, curved. The intermediate segment 380 may be sized and shaped such that it maximizes the amount of bone and/or tissue to prevent pull-out of the implant 300. The intermediate segment 380 may be sized and shaped (or otherwise configured) to form a gap from bone and/or tissue such that a surgeon feels the positive force of clearing the positive force of clearing the first segment 310 and the second segment 340. The neck 382 may have a diameter smaller than the diameter of the first segment 310 and the second segment 340. As shown in FIGS. 14 and 15, the intermediate segment 380 may be angled, for example, the second tapered section 386 may be angled with respect to the first tapered section 384. As also shown in FIG. 14, the implant 300 may be configured such that the first and second segments 310, 340 (or the axes thereof) are offset or angled along the longitudinal axis or direction of the implant 300 (i.e., are not collinear along the longitudinal axis or direction). Similarly, the implant 300 may be configured such that the first segment 310 and the intermediate segment 380 (or the axes thereof) are offset or angled along the longitudinal axis or direction of the implant 300 (i.e., are not collinear along the longitudinal axis or direction). For example, the first segment 310 may be angled from the intermediate segment 380 with respect to a longitudinal axis of the intermediate segment 380 or the second segment 340.

Referring now to FIGS. 18-22, another bone fixation implant 400 is shown. The bone fixation implant 400 is substantially similar to the implant 100 of FIGS. 1-7, implant 200 of FIGS. 8-11 and implant 300 of FIGS. 12-17, and therefore the same reference numerals or like reference numerals preceded by the numeral "4" are used to indicate like elements, functions, aspects or the like (and therefore the corresponding description thereof, including alternative embodiments, presented above with respect to the implant 100 of FIGS. 1-7, implant 200 of FIGS. 8-11 and implant 300 of FIGS. 12-17 may equally apply to implant 400 of FIGS. 18-22).

The implant 400 may have a first end 402 and a second end 404. The implant may also include a first portion or segment 410 near the first end 402 and a second portion or segment 440 near the second end 404. The first segment 410 and the second segment 440 may be, for example, coupled together with an intermediate portion or segment 480.

With continued reference to FIGS. 18-22, the first segment 410 may be of the type described above with reference to the first segment 310 and may include, for example, an insertion tip 312 at the first end 402 and a body portion 320 adjacent to the insertion tip 312. The insertion tip 312 may include a plurality of side portions 314 extending between a plurality of tips 316 at the first end 402, as described above with reference to implant 300 and FIGS. 12-17, which will not be described again here for brevity sake. The body portion 320 may include a plurality of side portions 322 extending between a plurality of tips 324 and at least one barb or ridge 326 inset into the body portion 320, as described above with reference to implant 300 and FIGS. 12-17, which will not be described again here for brevity sake. The at least one barb 326 may include an engagement portion 328 and a tapered portion 330, which are described in greater detail above with reference to implant 300 and which will not be described again here for brevity sake.

Figure 18:
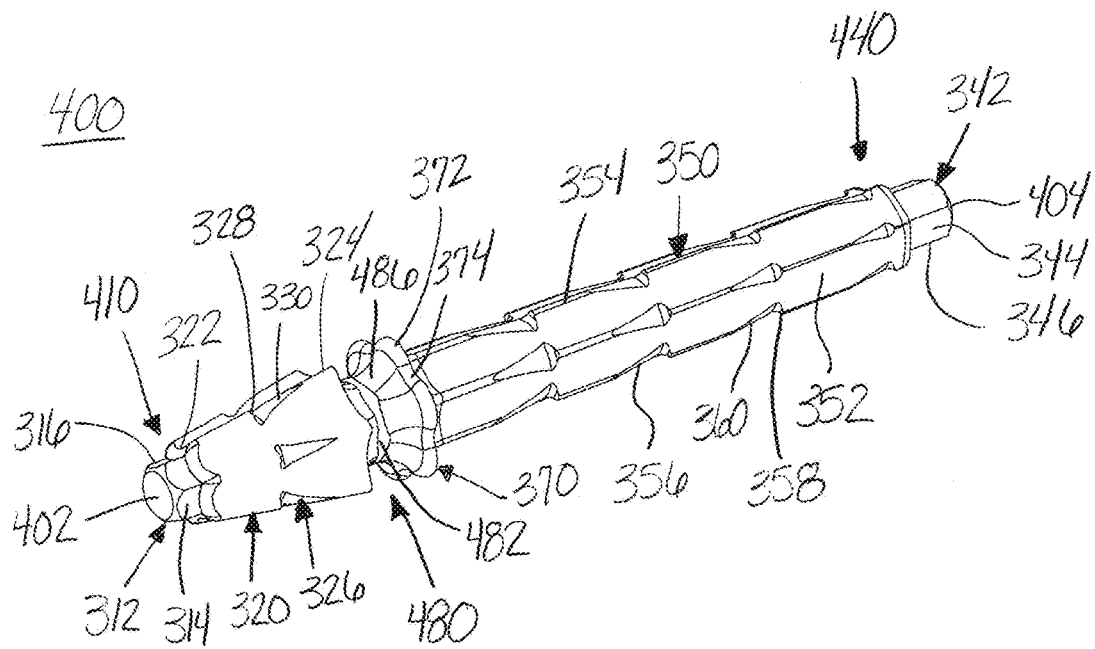
FIG. 18 is a front perspective view of yet another interphalangeal implant, in accordance with an aspect of the present invention.
Figure 19:
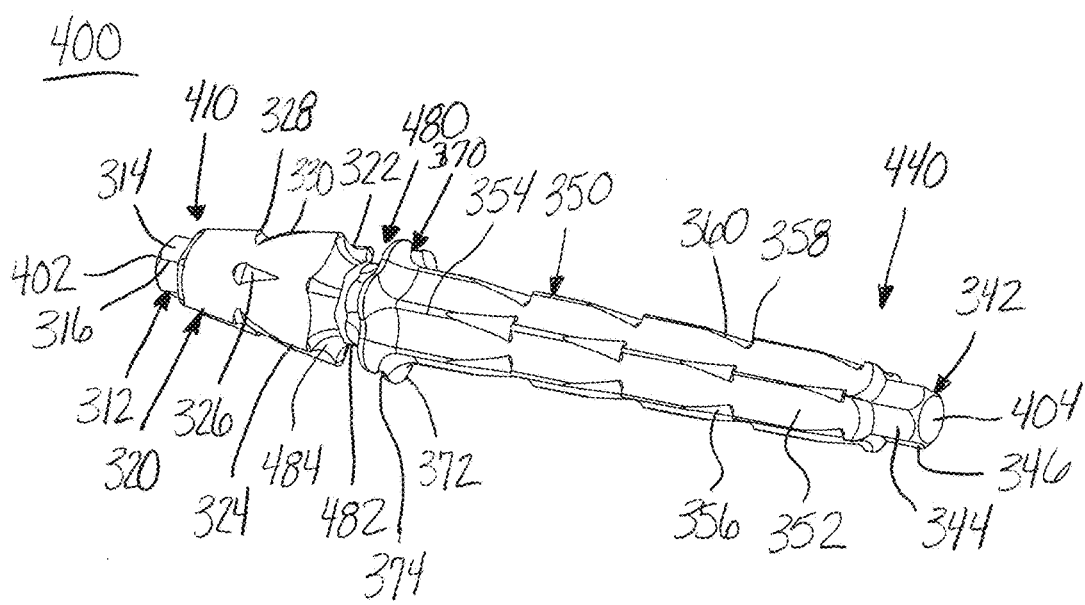
FIG. 19 is a rear perspective view of the implant of FIG. 18, in accordance with an aspect of the present invention.
Figure 20:
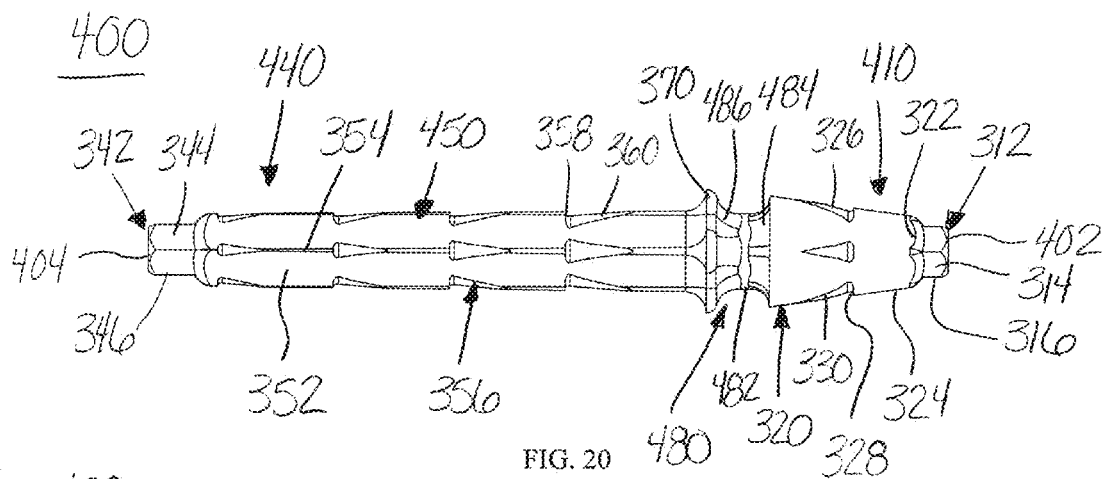
FIG. 20 is a side view of the implant of FIG. 18, in accordance with an aspect of the present invention.
Figure 21:
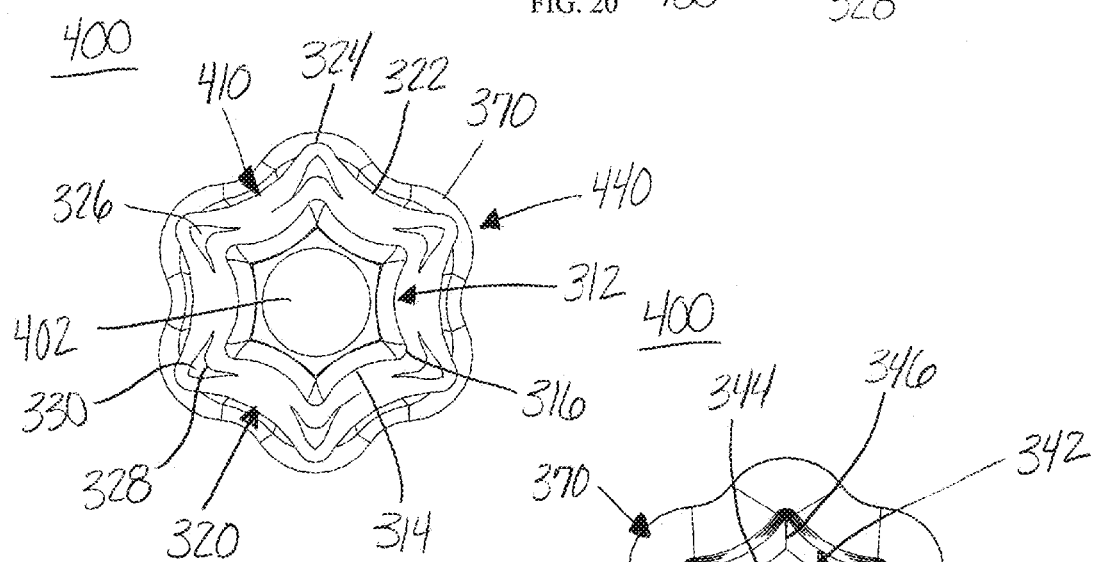
FIG. 21 is a front view of the implant of FIG. 18, in accordance with an aspect of the present invention.
Figure 22:
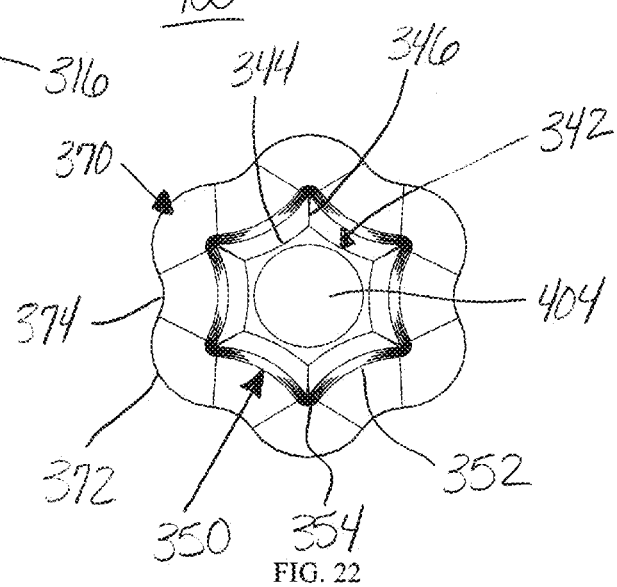
FIG. 22 is a rear view of the implant of FIG. 18, in accordance with an aspect of the present invention.
Figure 23:
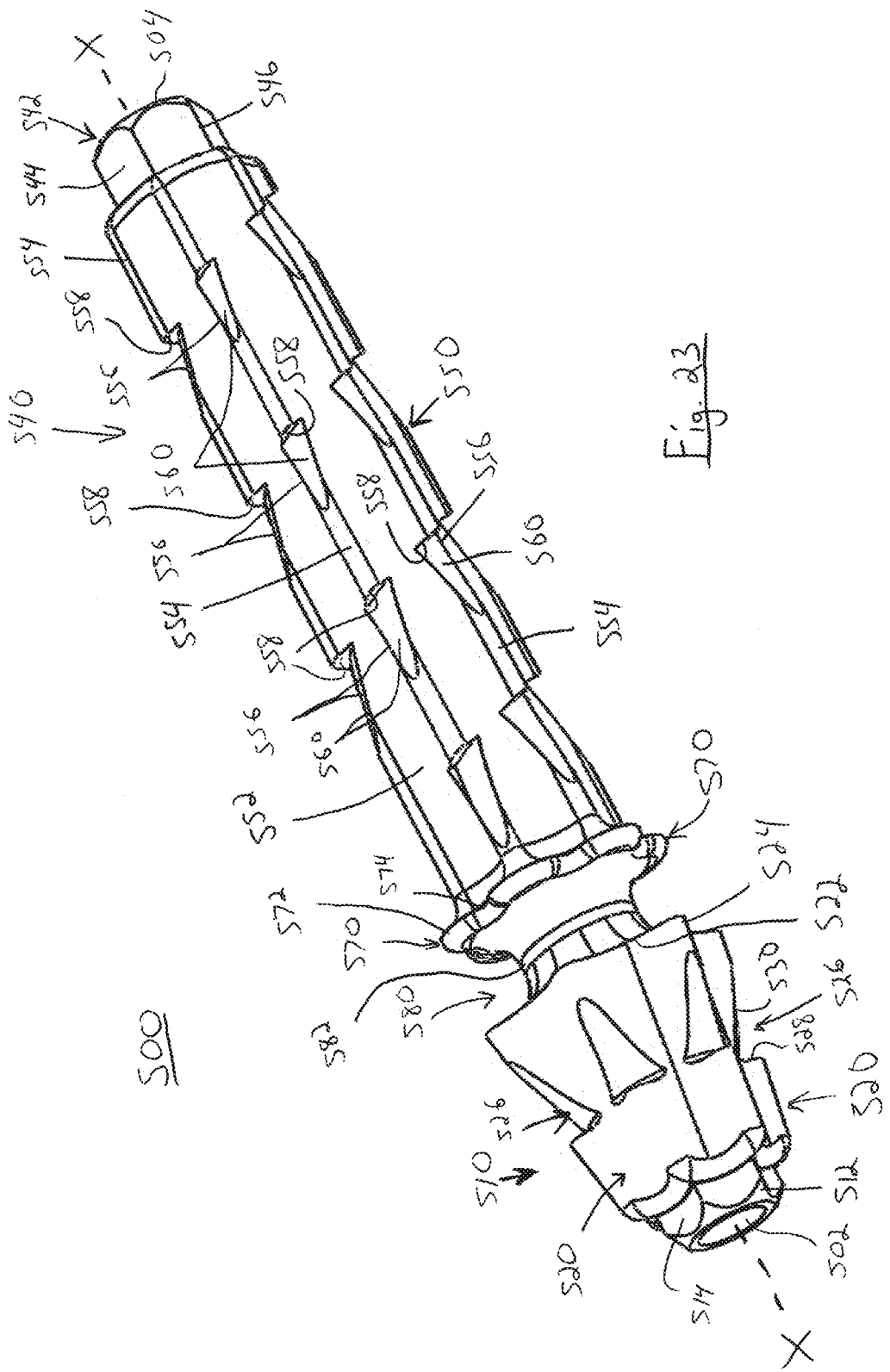
FIG. 23 is a rear perspective view of an interphalangeal implant, in accordance with an aspect of the present invention.
Figure 24:
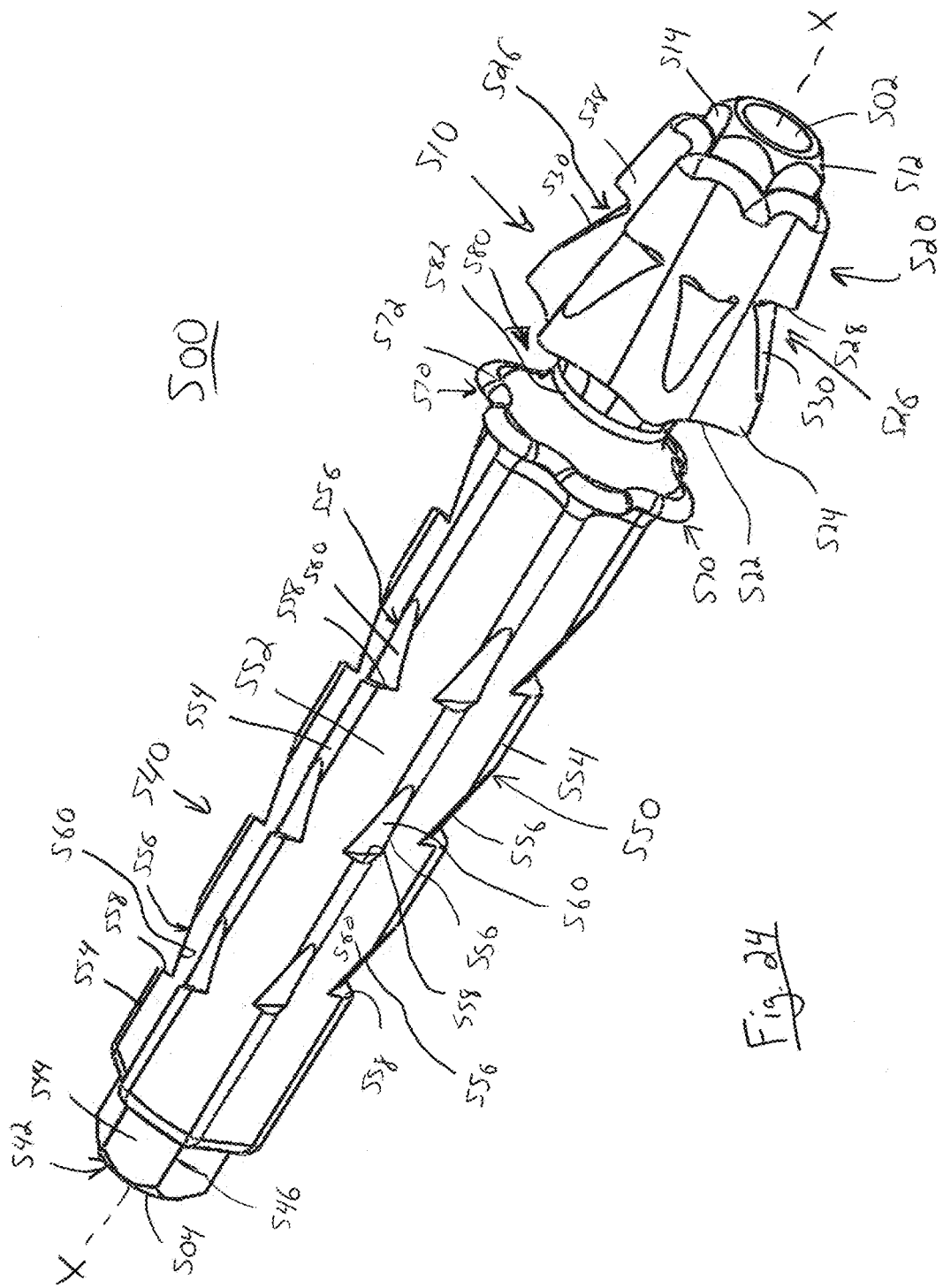
FIG. 24 is another rear perspective view of the implant of FIG. 23, in accordance with an aspect of the present invention.
Figure 25:
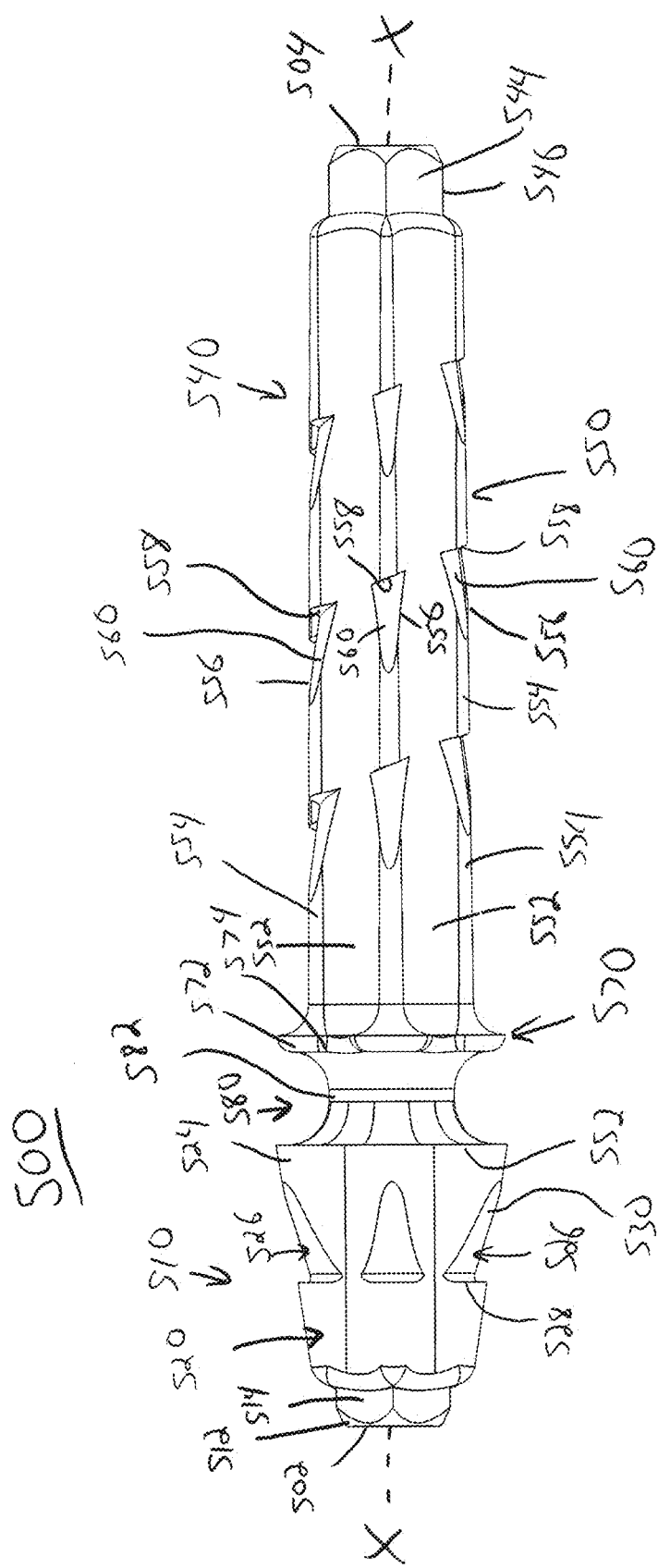
FIG. 25 is a side view of the implant of FIG. 23, in accordance with an aspect of the present invention.
Figure 26:
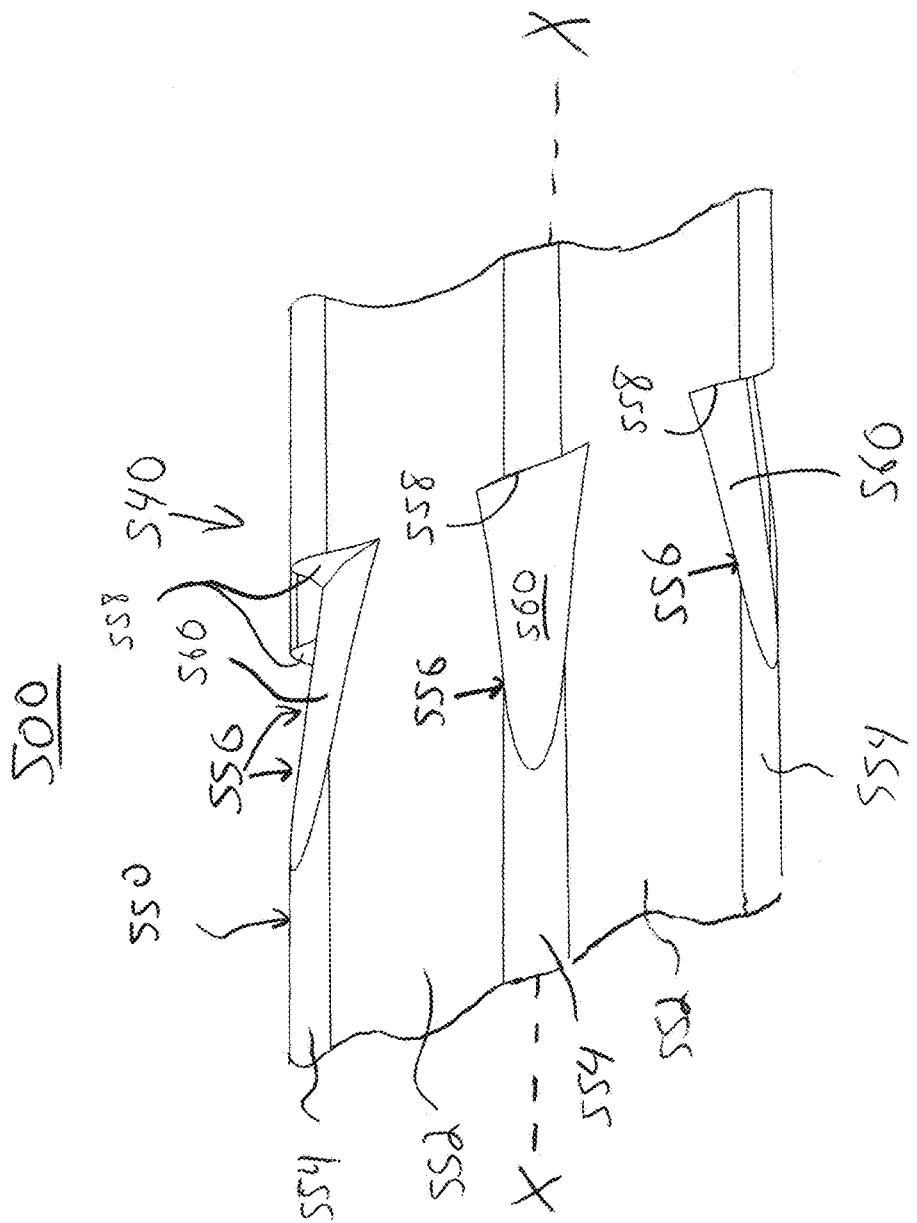
FIG. 26 is an enlarged side view of a portion of the implant of FIG. 23, in accordance with an aspect of the present invention.
Figure 27:
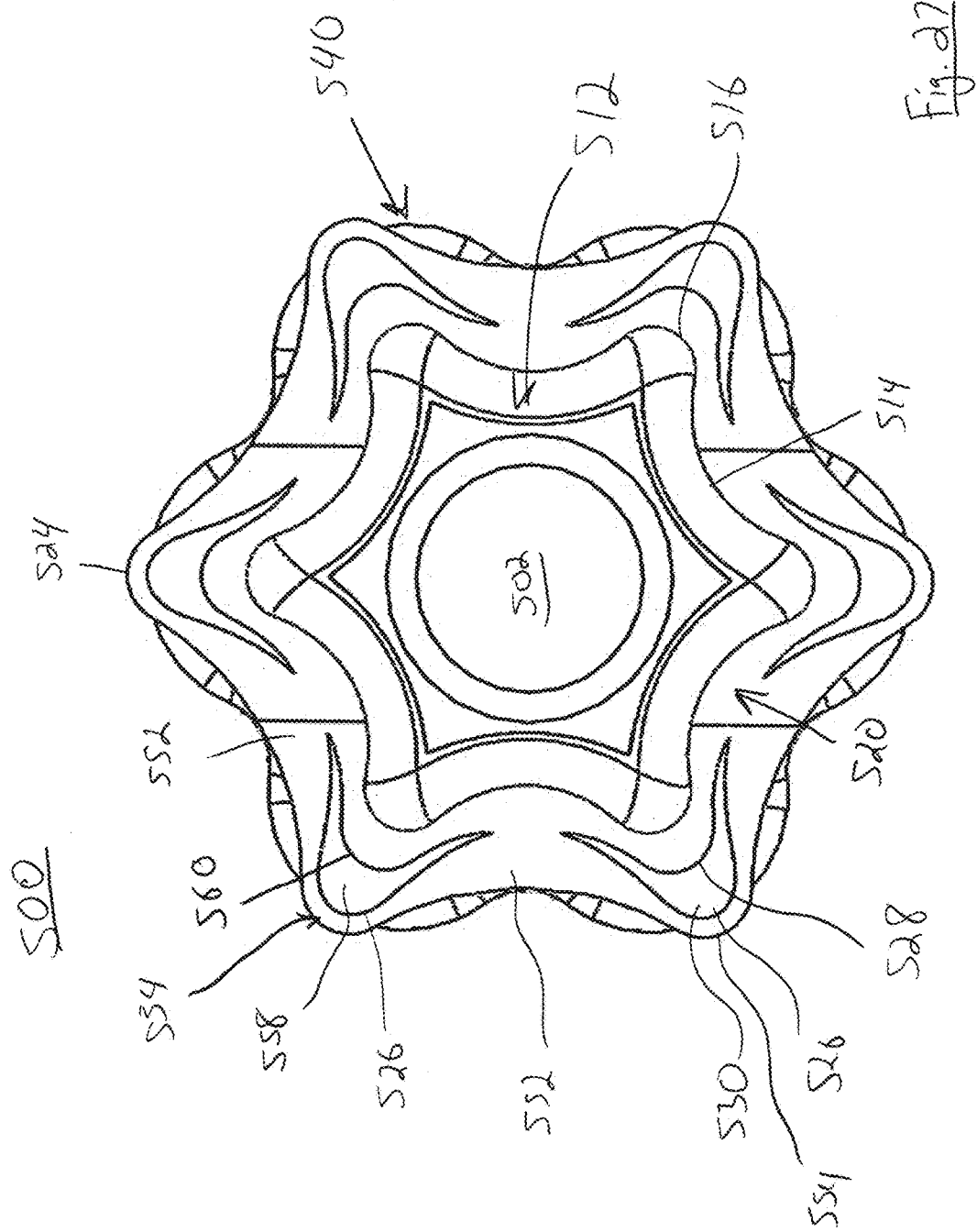
FIG. 27 is a front view of the implant of FIG. 23, in accordance with an aspect of the present invention.

The second segment 440 may be of the type described above with reference to the second segment 340 and may include, for example, an end member 342 at the second end 404 and a body portion 350 adjacent to the end member 342, as shown in FIGS. 18-20. The end member 342 may include a plurality of side portions 344 extending between a plurality of tips 346, as described above with reference to implant 300 and FIGS. 12-17. The body portion 350 may include a plurality of side portions 352 extending between a plurality of tips 354 and at least one barb or ridge 356 inset into the body portion 350, as described above with reference to implant 300 and FIGS. 12-17, which will not be described again here for brevity sake. The at least one barb 356 may include an engagement portion 358 and a tapered portion 360, which are described in greater detail above with reference to implant 300 and which will not be described again here for brevity sake. The second segment 440 may also include a stop member 370 near the first end 402 of the implant 400, as shown in FIGS. 18-20. The stop member 370 may include a plurality of lobes 372 and a plurality of channels 374 positioned between each lobe 372 and may be of the type described above with reference to implant 300 and will not be described again here for brevity sake.

The intermediate segment 480 may include a neck 482, a first tapered section 484 and a second tapered section 486. The first tapered section 484 may be positioned between the first segment 410 and the neck 482 and the second tapered section 486 may be positioned between the neck 482 and the second segment 440, as shown in FIG. 20. The first tapered section 484 may be, for example, tapered from the outer surface of an end of the first segment 410 to the neck 482 and the taper may be, for example, curved. In other embodiments, the first tapered section 484 may be flat or linear (e.g., a 90-degree straight section). The second tapered section 486 may be, for example, tapered from the outer surface of a second side of the stop member 370 of the second segment 440 to the neck 482 and the taper may be, for example, curved. In other embodiments, the second tapered section 486 may be flat or linear (e.g., a 90-degree straight section). The neck 482 may have a diameter smaller than the diameter of the first segment 410 and the second segment 440. As shown in FIG. 20, the intermediate segment 480 is aligned along a longitudinal axis with the first and second segments 410, 440.

Referring now to FIGS. 23-27, another bone fixation implant 500 is shown. The bone fixation implant 500 is substantially similar to the implant 100 of FIGS. 1-7, implant 200 of FIGS. 8-11, implant 300 of FIGS. 12-17 and implant 400 of FIGS. 18-22, and therefore the same reference numerals or like reference numerals preceded by the numeral "5" are used to indicate like elements, functions, aspects or the like (and therefore the corresponding description thereof, including alternative embodiments, presented above with respect to the implant 100 of FIGS. 1-7, implant 200 of FIGS. 8-11, implant 300 of FIGS. 12-17 and implant 400 of FIGS. 18-22 may equally apply to implant 500 of FIGS. 23-27). The implant 500 may differ from the implants 100, 200, 300 and 400 in the orientation of the engagement portion 558 of the barbs 556 of the body portion 550 of the second segment or portion 540.

As discussed above and shown in FIGS. 23-27, the body portion 550 may include at least one barb or ridge 556 inset into the body portion 550. The at least one barb 556 may be, for example, positioned in each tip portion 554. The at least one barb 556 may include an engagement portion 558 and a tapered portion 560. The engagement portion 558 may be sized and shaped for maximum contact with the intramedullary canal of the phalange to prevent of the pull out of the implant 500. The engagement portion 558 may be positioned, for example, closer to the second end 504 than the tapered portion 560. The engagement portion 558 may be planar, arcuate, convex, concave or angled (as discussed below). The tapered portion 560 may taper from the engagement portion 558 longitudinally toward the first end 502. The larger the taper of the tapered portion 560, the more bone and/or tissue the corresponding engagement portion 558 of each barb 556 may engage. The tapered portion 560 may extend into the interior of the implant 500 to any degree. In some embodiments, the tapered portion 560 may extend toward the interior of the implant 500 to a lesser extent than the neck 582 of the intermediate segment 580. As shown in FIGS. 23-27, a plurality of barbs 565 may be provided in each tip portion 554.

The plurality of barbs 565 of each tip portion 554 may be spaced longitudinally, such as within the range of about 1 mm to about 5 mm. In some embodiments, the plurality of barbs 565 of each tip portion 554 may be spaced longitudinally about 3 mm.

As opposed to the normal or perpendicular arrangement or orientation of the engagement portions of the at least one barb of the implants 100, 200, 300 and 400 with respect to the longitudinal direction or axis, the engagement portion 558 of the least one barb 556 of the implant 500 is angled with respect to the longitudinal direction or axis X-X as shown in FIGS. 23-27. As shown in FIGS. 23-27, the engagement portion 558 of the least one barb 556 extends toward the first end 502 or the first end 504 (depending upon the point of reference) as it extends about the longitudinal axis or along the width of the implant 500. Stated differently, the engagement portion 558 of the least one barb 556 extends toward the first end 502 or the second end 504 (depending upon the point of reference) as it extends laterally across the implant 500 in a width direction. The engagement portion 558 may or may not also extend toward the first end 502 or the second end 504 as it extends radially toward the longitudinal axis X-X of the implant 500 to the corresponding engagement portion 558.

In this way, at least the engagement portions 558 of the barbs 556 are provided in a thread-like or helical-like design/pattern across the surface of the implant 500 that facilitates twisting or rotation of the implant 500 about the axis X-X after implantation. After implantation and rotation, the tip portions 554, and thereby the engagement portion 558 of the least one barb 556 provided therein, are positioned proximate to or in line (in the longitudinal direction) with bone and/or tissue that has not been removed or otherwise damaged, disturbed or weakened during implantation (such as longitudinal implantation) of the implant 500 (such as via the tip portions 554 and/or the barbs 556). Therefore, when/if the implant is affected by a pull-out force along the longitudinal axis X-X, the barbs 556 are re-positioned proximate to or in line with native bone and/or tissue which improves the pull-out resistance of the implant 500 along the longitudinal axis X-X (as compared to prior to rotation).

The implants 100, 200, 300, 400 and 500 may be, for example, made of a medical grade titanium. Other suitable materials may be used as well such as other metals and/or other polymers, ceramics or composites. The implants 100, 200, 300, 400 and 500 may also be formed, for example, using additive manufacturing methods. The implants 100, 200, 300, 400 and 500 may include, for example, a surface roughness and geometry for osteosynthesis in an intramedullary canal between a first phalange and a second adjacent phalange. The implants 100, 200, 300, 400 and 500 may be cannulated. For example, the linear implants 200, 400 and 500 (i.e., the first and second segments being collinear or aligned along the longitudinal direction or axis) may be cannulated along the longitudinal direction or axis to aid in implantation.

A method of insertion of the implants 100, 200, 300, 400 and 500 may include, for example, insertion of the implants 100, 200, 300, 400 and 500 between a first phalange and a second phalange adjacent to the first phalange. In one example, the first phalange may be the proximal phalange and the second phalange may be the intermediate phalange, which exists at the proximal interphalangeal joint. As noted above, if the engagement portions of the barbs of the tip portions are angled in a thread- or helical-like fashion, the implant 100, 200, 300, 400 or 500 may be twisted or rotated about the longitudinal axis X-X after insertion into bone and/or tissue, such as after longitudinal insertion into a canal of the first phalange or the second phalange. The layout or position of the tip portions 554 (and thereby the barbs 556 therein) about the longitudinal axis X-X may dictate the necessary rotation of the implant 100, 200, 300, 400 or 500 about the longitudinal axis X-X after insertion into bone and/or tissue such that the barbs 556 are re-positioned proximate to or in line with native bone and/or tissue. In some embodiments, the implant 100, 200, 300, 400 or 500 may be twisted or rotated about the longitudinal axis X-X about 15 degrees after insertion into bone and/or tissue.

Figure 28:
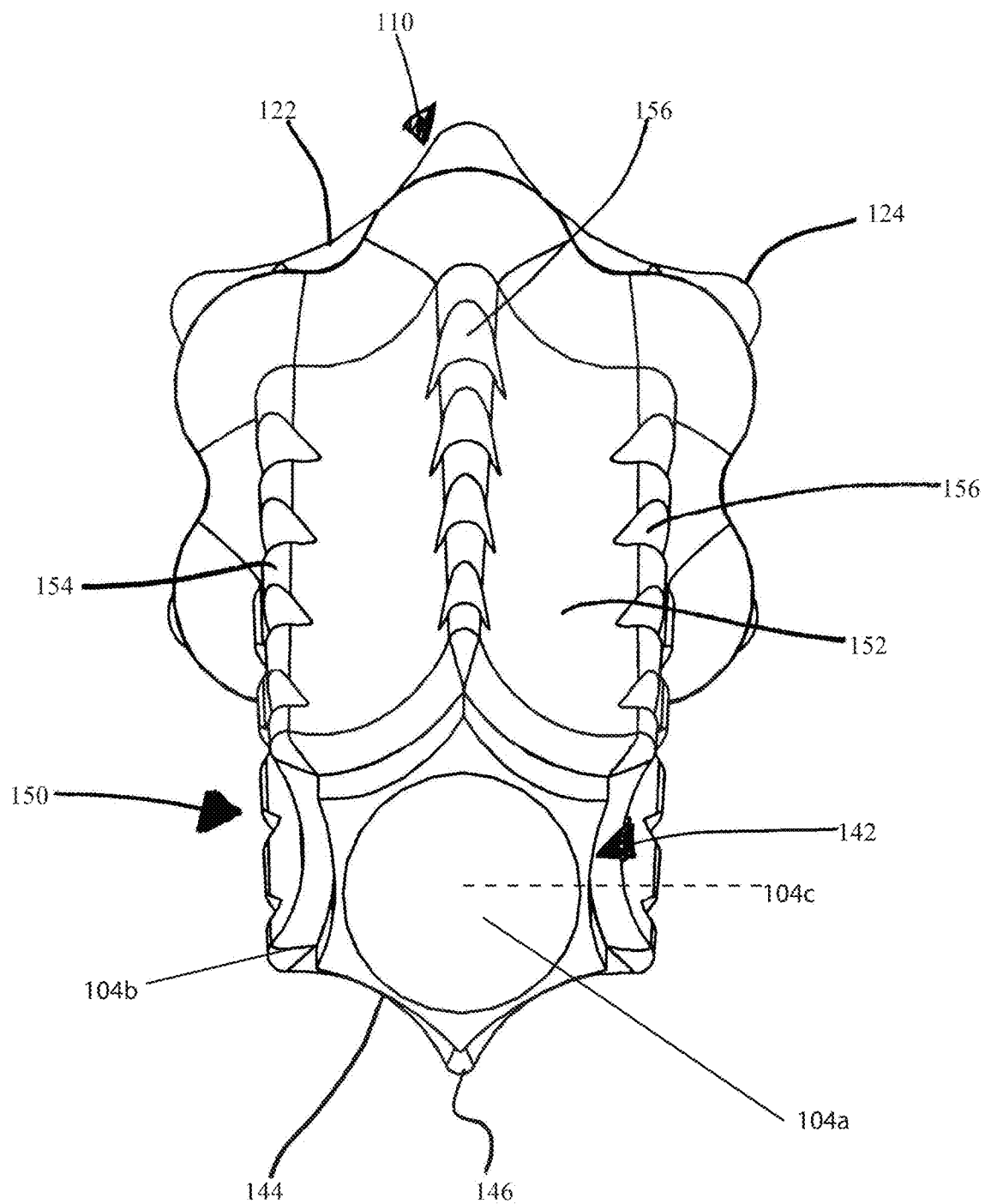
FIG. 28 is a view of another embodiment including an implant having a different core and shell structure.

FIG. 28 shows another embodiment of an implant 100 which includes a first portion or segment 110 having side portions 122 and a plurality of tips 154. There is also a body portion, which has a shell 104b and a core 104a. The shell 104b forms the side portions 122, 144, 152 tips 124, 146, 154, a barb or ridge 156. The core 104a runs through the end member 142 as well as the first portion or segment 110, the intermediate portion or segment 180 and the second portion or segment 140 as well. As discussed above, the core 104a of any one of the first segment 110, the second segment 140 or the intermediate segment 180 can be made from solid material while the shell 104b is made from a porous structure or a honeycomb structure. Alternatively, the shell 104b can be made from a solid material while the core 104a is made from a porous lattice material. There is also a radial axis 104c which radiates out from a central core 104a as well.

Figure 29:
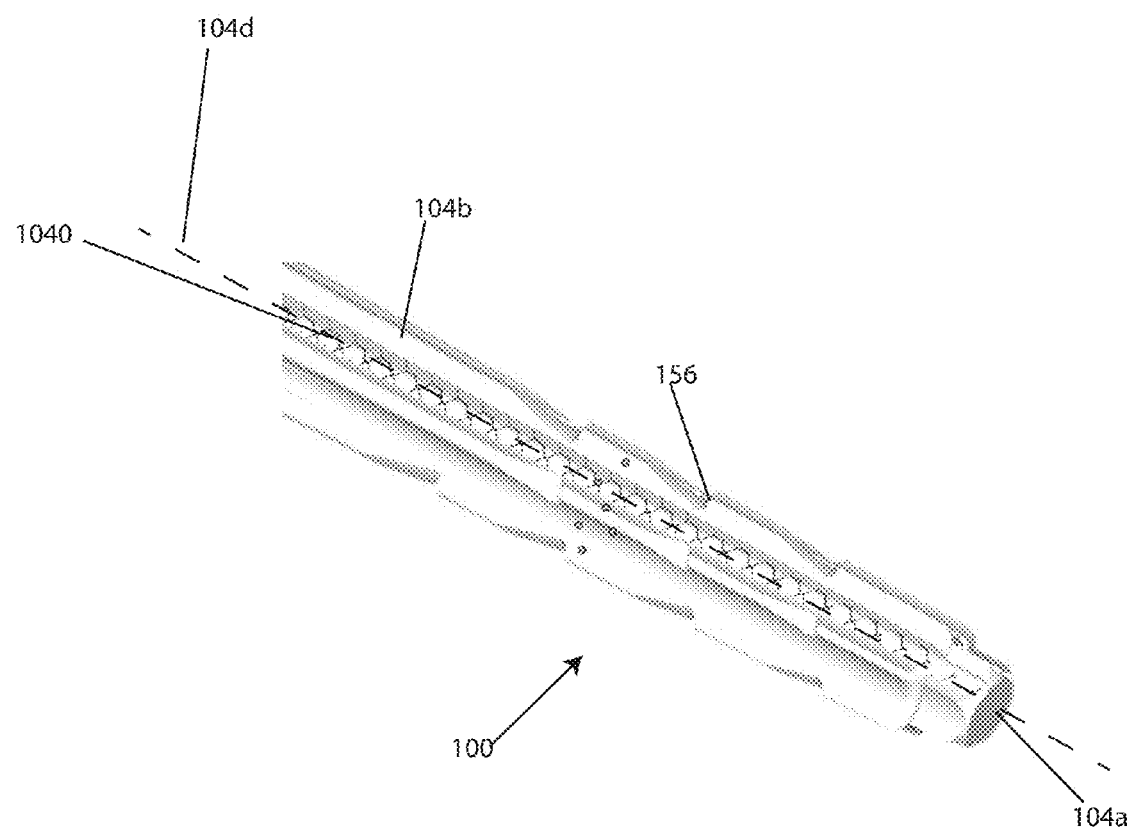
FIG. 29 is a side cross-sectional view of the embodiment of FIG. 28.
Figure 30:
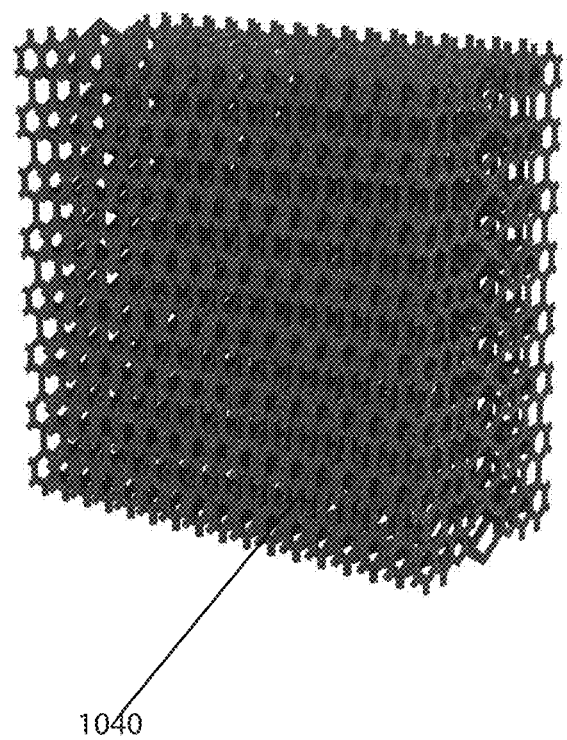
FIG. 30 is a perspective view of the lattice structure.

FIG. 29 shows an embodiment of an implant wherein the core 104a is made from a lattice or porous material while the shell 104b is made from a solid material. This lattice structure 1040 is shown in greater detail in FIG. 30, which shows a cross-section of a typical porous lattice structure. The implant is shown extending along a longitudinal axis 104d which extends transverse to the radial axis 104c.

Figure 31:
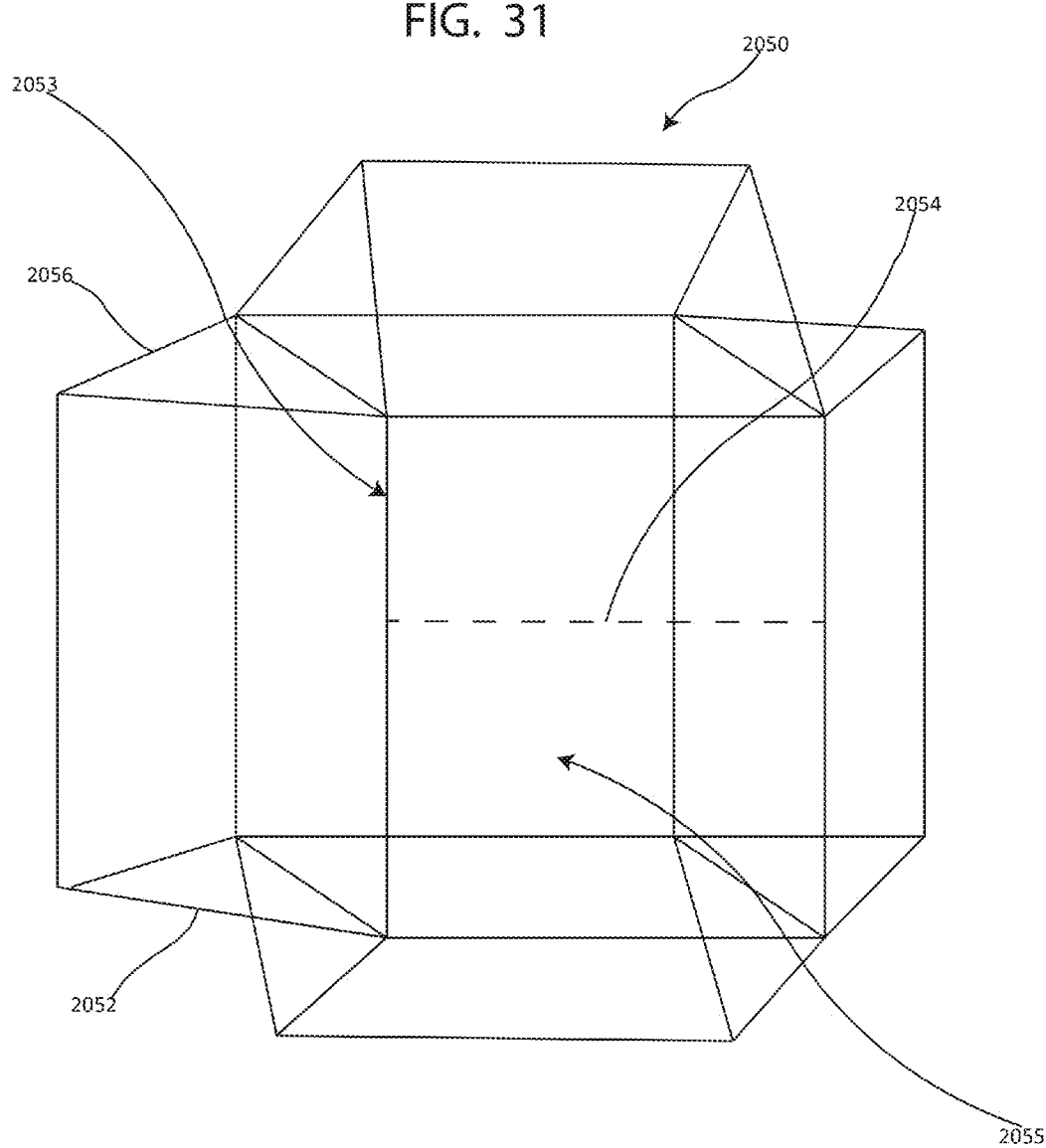
FIG. 31 is a view of the honeycomb structure.

One example of the lattice structure shape is a honeycomb structure shown in greater detail in FIG. 31. In this view, there is shown a single cell 2050 of a honeycomb structure having a central cube 2053 having a square cross-section 2055. This cross-section 2055 has a pore or opening 2054 which allows for the ingress of material such as bone growth material to aid in the growth of bones as the bones knit together. Along with the central cube are lattice structures having a triangular cross-section 2056. This structure 2056 has a plurality of different struts supporting the overall shape. While a honeycomb type structure is shown, other alternative structures can also be used as well or as is appropriate.

Figure 32:
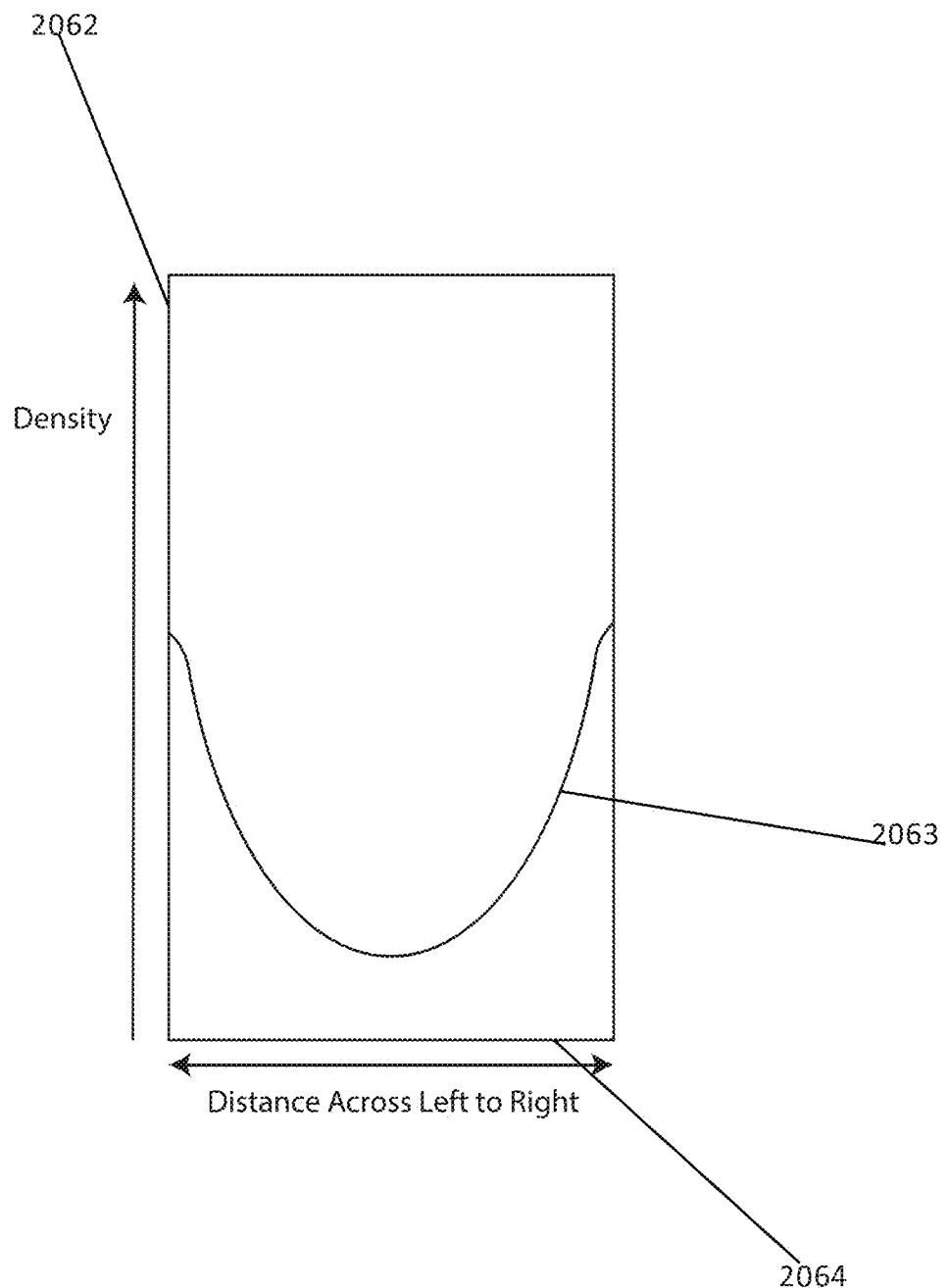
FIG. 32 is a view of the profile of the different porosity profiles for the implant.

In addition, while the core 104a or the shell 104b is shown, the porosity of the core or shell can be varied or the porosity of the entire device can be varied either along its longitudinal axis 104d or as a function of its radial position radiating out from a central core along radial axis 104c in core 104a. For example, there is shown in FIG. 32 an example of a porosity profile which has a Y axis 2062 which tracks the density of the lattice structure. The X axis of this graph is the distance across the device either along the longitudinal axis 104d of an insert such as with implant 100 or as a function radiating out along radial axis 104c from a central region on a central core such as starting from central core 104a. The density or porosity profile can vary such as the implant can become more dense towards the center of the implant, or alternatively the porosity profile can be such that the implant becomes less dense towards the center of the implant as well. The above porosity structure also applies to the different embodiments of the implants such as implants 200, 300, 400 and 500.

In one embodiment, the implant 100 or the other identified implants 200, 300, 400 or 500 may include a constant or varying porosity, within the range of about 60% to about 90%, or within the range of about 65% to about 85%, or within the range of about 70% to about 80%. The porous architecture of the implant 100 may be a defined or uniform architecture or a pattern, may be a randomly generated or distributed architecture or lattice, or may include a different architecture in differing portions of the implant 100.

In other embodiments, the porosity can range more widely such as between a 0% porous architecture to a 70% porous architecture such that the difference in porosity between the most porous region and the least porous region can be as much as 70%. In at least another embodiment, the difference in porosity between the most porous region and the least porous region can be as much as 50%. Of course, the above identified embodiments are configured to provide for any variation between the above percentage differences between 70% and 5%.

Ultimately, while no absolute overall values are given based upon the overall changes in size of the pores or holes, the change in porosity or density could be between 5-90% in at least one embodiment, or between 1-75% in at least another embodiment. In another embodiment, the change in density could be 30%, while in other embodiments the change in density could be any one of substantially 20%, 30%, 40%, 50%, 60%, 70%, or 80%. These differences in density can be customized based upon the location of the device being implanted as well as the thickness of the bone, the bone structure adjacent to the implant, the movement and loading conditions as well. The shape and porosity profiles of these embodiment(s) is supported by U.S. provisional application 62/404,923 filed on Oct. 6, 2016 the disclosure of which is hereby incorporated by reference in its entirety.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

As may be recognized by those of ordinary skill in the art based on the teachings herein, numerous changes and modifications may be made to the above-described and other embodiments of the present invention without departing from the scope of the invention. The first segments, second segments, intermediate segment, and other components of the device and/or system as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices and systems may include more or fewer components or features than the embodiments as described and illustrated herein. For example, the components and features of FIGS. 1-7, FIGS. 8-11, FIGS. 12-17, and FIGS. 18-22 may all be used interchangeably and in alternative combinations as would be modified or altered by one of skill in the art. Accordingly, this detailed description of the currently-preferred embodiments is to be taken in an illustrative, as opposed to limiting of the invention.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

The invention claimed is:

1. An interphalangeal implant for insertion between a patient's interphalangeal joints, comprising:

a first elongated anchoring segment at a first end of the implant, said first elongated anchoring segment being substantially frustoconical in shape and having an insertion tip at the first end of the implant and a body portion adjacent to the insertion tip, wherein the insertion tip extends out from the body portion, wherein said insertion tip includes a plurality of side portions which are curved towards a center of the first elongated anchoring segment;

a second elongated anchoring segment at a second end of the implant, said second elongated anchoring segment being substantially cylindrical and having an end member at the second end of the implant and a body portion adjacent to the end member, wherein the end member extends out from the body portion of the second elongated anchoring segment, wherein said second elongated anchoring segment has a plurality of longitudinally-extending tip portions spaced about a longitudinal axis of the second elongated anchoring segment and a plurality of longitudinally-extending side portions which are curved toward a center of the second elongated anchoring segment, wherein the plurality of longitudinally-extending side portions of the second elongated anchoring segment extend between the plurality of longitudinally-extending tip portions to form a polygonal shape in cross-section; and an intermediate segment comprising a first tapered portion coupled to the first elongated anchoring segment on a first end, a second tapered portion coupled to the second elongated anchoring segment on a second end, a neck positioned between and coupled to the first tapered section and the second tapered section, and a plurality of side portions which are curved towards a center of the intermediate segment, wherein each of the plurality of longitudinally-extending tip portions includes a series of barbs, each barb formed by a taper portion and an engagement portion extending radially into the tip portion, wherein a maximum diameter of the intermediate segment being less than a maximum diameter of each of the first and second elongated anchoring segments, wherein a length of the first elongated anchoring segment ranges from about 3 mm to about 6 mm, a length of the second elongated anchoring segment ranges from about 9 mm to about 17 mm, and a length of the intermediate segment ranges from about 1 mm to about 2 mm, wherein the intermediate segment is angled from the first elongated anchoring segment with respect to the longitudinal axis of the second elongated anchoring segment, wherein the first elongated anchoring segment is sized and shaped for anchoring within an intramedullary canal of a first phalange, and wherein the second elongated anchoring segment is sized and shaped for anchoring within an intramedullary canal of a second adjacent phalange.

2. The interphalangeal implant of claim 1, wherein the second elongated anchoring segment further comprises:

a stop member near a first end of the second elongated anchoring segment.

3. The interphalangeal implant of claim 1, wherein the implant has a core section and a shell section, wherein at least one of said core section and said shell section is porous.

4. The interphalangeal implant of claim 1, wherein the engagement portion of each barb of said series of barbs is oriented substantially normal to the longitudinal axis of the second elongated anchoring segment.

5. The interphalangeal implant of claim 1 wherein the engagement portion of each barb of said series of barbs is angled towards one of the first and second ends of the implant as is extends about the longitudinal axis of the second elongated anchoring segment.

6. The interphalangeal implant as in claim 1, wherein said series of barbs are positioned on said second elongated anchoring segment in a helical pattern.

7. The interphalangeal implant as in claim 6, wherein at least one of the first and second elongated anchoring segments is configured to be twisted or rotated about its longitudinal axis at least 15 degrees after implantation of the interphalangeal implant to secure the implant in a person's body.

8. The interphalangeal implant as in claim 1, wherein at least one surface on at least one the first elongated anchoring segment and the second elongated anchoring segment is roughened.

* * * * *